United States Patent
Neal et al.

(10) Patent No.: US 12,245,972 B2
(45) Date of Patent: Mar. 11, 2025

(54) SYSTEM AND METHODS FOR CUSTOMIZING AN INTRAOCULAR LENS USING A WAVEFRONT ABERROMETER

(71) Applicants: Daniel R. Neal, Tijeras, NM (US); R. James Copland, Albuquerque, NM (US); Xifeng Xiao, Albuquerque, NM (US); Alan Blair, Albuquerque, NM (US)

(72) Inventors: Daniel R. Neal, Tijeras, NM (US); R. James Copland, Albuquerque, NM (US); Xifeng Xiao, Albuquerque, NM (US); Alan Blair, Albuquerque, NM (US)

(73) Assignee: WaveFront Dynamics, Inc., Albuquerque, NM (US)

( * ) Notice: Subject to any disclaimer, the term of this patent is extended or adjusted under 35 U.S.C. 154(b) by 528 days.

(21) Appl. No.: 17/325,168

(22) Filed: May 19, 2021

(65) Prior Publication Data
US 2021/0267799 A1 Sep. 2, 2021

Related U.S. Application Data

(60) Provisional application No. 63/085,391, filed on Sep. 30, 2020, provisional application No. 63/027,428, filed on May 20, 2020.

(51) Int. Cl.
*A61F 9/008* (2006.01)
*A61B 3/00* (2006.01)
(Continued)

(52) U.S. Cl.
CPC ........ *A61F 9/00804* (2013.01); *A61B 3/0025* (2013.01); *A61B 3/0041* (2013.01);
(Continued)

(58) Field of Classification Search
CPC .......... A61F 9/00804; A61F 2009/0087; A61F 2009/00872; A61F 2009/0088;
(Continued)

(56) References Cited

U.S. PATENT DOCUMENTS 5,430,509 A   7/1995  Kobayashi
5,777,719 A   7/1998  Williams
(Continued)

FOREIGN PATENT DOCUMENTS

WO   WO 1999027334   3/1999
WO   WO 04072709     12/2004
WO   WO 2010019885   2/2010

OTHER PUBLICATIONS

C. Kraff, R. Maloney, and S. Coleman, "Clinical and patient reported outcomes after wavefront-guided LASIK for myopia using a high definition Hartmann Shack Aberrometer", ASCRS 23_2018.
(Continued)

*Primary Examiner* — Scott M. Getzow
(74) *Attorney, Agent, or Firm* — Quinn IP Law

(57) ABSTRACT

A method and system for correcting vision in an eye that uses a wavefront-customized phakic or pseudophakic Intraocular Lens (IOL), the method comprising: (1) measuring wavefront aberrations of the eye; (2) designing a wavefront-customized correction profile for an IOL; (3) creating a customized IOL with the customized correction profile; and (4) implanting the customized IOL in the eye, without having to remove the natural lens. Alternatively, an uncorrected IOL is implanted first, followed by scanning a femtosecond laser spot across the implanted IOL to locally change the Index of Refraction of the IOL material and create an in-situ customized IOL.

30 Claims, 20 Drawing Sheets

(51) Int. Cl.
  *A61B 3/10* (2006.01)
  *A61B 3/103* (2006.01)
  *A61B 3/107* (2006.01)
  *A61B 3/15* (2006.01)

(52) U.S. Cl.
  CPC ............ *A61B 3/101* (2013.01); *A61B 3/1015* (2013.01); *A61B 3/102* (2013.01); *A61B 3/103* (2013.01); *A61B 3/107* (2013.01); *A61B 3/158* (2013.01); *A61F 2009/0087* (2013.01); *A61F 2009/00872* (2013.01); *A61F 2009/0088* (2013.01); *A61F 2009/00882* (2013.01)

(58) Field of Classification Search
  CPC ......... A61F 2009/00882; A61B 3/0025; A61B 3/0041; A61B 3/101; A61B 3/1015; A61B 3/102; A61B 3/103; A61B 3/107; A61B 3/158
  See application file for complete search history.

(56) References Cited

U.S. PATENT DOCUMENTS

| | | |
|---|---|---|
| 5,949,521 A | 9/1999 | Williams |
| 6,086,204 A | 7/2000 | Magnante |
| 6,095,651 A | 8/2000 | Williams |
| 6,299,311 B1 | 10/2001 | Williams |
| 6,379,008 B1 | 4/2002 | Chataeu |
| 6,499,843 B1 | 12/2002 | Cox |
| 6,511,180 B2 | 1/2003 | Guirao |
| 6,550,917 B1 | 4/2003 | Neal |
| 6,554,425 B1 | 4/2003 | Roffman |
| 6,634,750 B2 | 10/2003 | Neal |
| 6,655,803 B1 | 12/2003 | Rubenstein |
| 6,830,712 B1 | 12/2004 | Roffman |
| 6,848,790 B1 | 2/2005 | Dick |
| 7,044,944 B2 | 5/2006 | Campin |
| 7,530,691 B1 | 5/2009 | Davis |
| 7,699,467 B2 | 4/2010 | Dick |
| 7,967,440 B1 | 6/2011 | Copland |
| 7,976,163 B2 | 7/2011 | Campbell |
| 7,980,699 B2 | 7/2011 | Neal |
| 8,197,064 B2 | 6/2012 | Copland |
| 8,260,024 B2 | 9/2012 | Farrer |
| 8,292,952 B2 | 10/2012 | Bille |
| 8,512,320 B1 | 8/2013 | Knox |
| 8,568,627 B2 | 10/2013 | Bille |
| 9,022,570 B2 | 5/2015 | Applegate |
| 9,023,257 B2 | 5/2015 | Sahler |
| 9,107,746 B2 | 8/2015 | Sahler |
| 9,186,242 B2 | 11/2015 | Sahler |
| 9,192,292 B2 | 11/2015 | Bille |
| 9,307,901 B1* | 4/2016 | Linhardt ............ A61B 5/14532 |
| 9,545,340 B1 | 1/2017 | Knox |
| 10,201,276 B2 | 2/2019 | Neal |
| 10,485,655 B2 | 11/2019 | Pinto |
| 10,492,680 B2 | 12/2019 | Farrer |
| 10,506,923 B2 | 12/2019 | Neal |
| 10,555,669 B2 | 2/2020 | Pulaski |
| 10,682,056 B2 | 6/2020 | Neal |
| 10,849,493 B2 | 12/2020 | Copland |
| 10,849,495 B2 | 12/2020 | Pulaski |
| 2003/0210378 A1* | 11/2003 | Riza ....................... A61B 3/066 351/205 |
| 2008/0001320 A1 | 1/2008 | Knox |
| 2008/0165324 A1* | 7/2008 | Lindacher ............... A61B 3/028 351/159.41 |
| 2009/0287306 A1 | 11/2009 | Smith |
| 2011/0230751 A1* | 9/2011 | Kersting ............... A61B 3/0025 600/407 |
| 2013/0310816 A1* | 11/2013 | Rathjen ................... A61F 9/008 606/4 |
| 2018/0243082 A1* | 8/2018 | Zheleznyak ........ A61F 9/00827 |
| 2019/0343683 A1 | 11/2019 | Zheleznyak |
| 2020/0107953 A1* | 4/2020 | Adler ..................... A61F 9/008 |

OTHER PUBLICATIONS

L. Zheleznyak, "First demonstration of human visual performance through refractive-index modified ophthalmic devices written in hydrogels," IOVS vol. 58(8) 1274-1274, (2017).

G. Gandara-Montano, "Optical bench testing of gradient-index Fresnel lenses written with femtosecond laser induced refractive index change," IOVS vol. 58(8), 1275-1275], (2017).

Blanton, US "Meta-analysis of six excimer laser platforms for safety and efficacy in myopic laser-assisted in situ keratomileusis," Ophthalmic Review vol. 8, Issue 1 Spring 2015.

Moussa, "Visual aberrometric photic patient satisfaction LASIK w high resolution aberrometer," Opth-10-2489, (2016).

E. Manche, "Wavefront-optimized versus wavefront-guided LASIK: One-year results of a contralateral eye study," ASCRS 26 2018.

B. Alqattan, A.K. Yetisen, H Butt, "Direct Laser Writing of Nanophotonic Structures on Contact Lenses", ACS Nano 2018, 12, 5030-5040.

X. He, et. al, Relative position of the central hole after EVO-ICL implantation for moderate to high myopia; BMC Ophthalmology (2020) 20:305.

S.C. Schallhorn et al., Wavefront-Guided Photorefractive Keratectomy with the Use of a New Hartmann-Shack Aberrometer in Patients with Myopia and Compound Myopic Astigmatism, Journal of Ophthalmology vol. 2015, Article ID 514837, 9 pages.

* cited by examiner

Conventional Iris Imaging System

Conventional Iris Imaging System

Dark-Field Iris Imaging System

Dark-Field Iris Imaging System

A. Before Laser Treatment, with Phakic IOL

B. During Laser Treatment

Eye Tracking System

SYSTEM AND METHODS FOR CUSTOMIZING AN INTRAOCULAR LENS USING A WAVEFRONT ABERROMETER

CROSS-REFERENCES TO RELATED APPLICATIONS

This application claims priority benefits of U.S. Provisional 63/027,428 filed May 20, 2020; and U.S. Provisional 63/085,391 filed Sep. 30, 2020, both of which are incorporated herein by reference in their entirety.

FIELD OF THE INVENTION

This invention relates to methods and devices that are used in optometry, ophthalmology, optical imaging, and aberrometry. In particular, the invention relates to phakic intraocular lenses (IOLs) that that are implanted into eye, where the natural crystalline lens has not been removed; and to pseudophakic IOLs, which are used when the natural lens is removed (usually due to the development of cataracts).

BACKGROUND OF THE INVENTION

LASIK surgery can correct myopia up to −12 D to −14 D. The higher the intended correction, the thinner and flatter the cornea will be post-operatively. Typically, phakic IOL's are used in place of LASIK laser surgery when the surgery would result in a corneal thickness that would be too thin to permit LASIK. For LASIK excimer laser surgery, one has to preserve a safe residual stromal bed thickness of at least 250 microns, preferably 300 microns. Below these limits, there is an increased risk of developing corneal ectasia (i.e., corneal forward bulging) due to thin residual stromal bed, which results in loss of visual quality. Due to the risk of generating higher order aberrations (HOA's), there is a current trend toward reducing the upper limits of LASIK and PRK to around −8 D to −10 D. Hence, the use of phakic intraocular lenses (IOLs) is a safer option than performing excimer laser surgery for those patients with significant myopia.

Phakic IOLs are currently made by Staar Surgical, AMO, and Ophtec. The Staar phakic IOL is named "Visian ICL™", and it is implanted between the iris and the natural crystalline lens. Visian ICL™ is made of soft, collamer material that is manufactured by Staar. The version most commonly used only corrects spherical errors (sphere), but is also available in a toric version, as well, for correcting astigmatism [U.S. Pat. No. 10,485,655].

The AMO phakic IOL is named "Veriseye™", and it is implanted in the anterior chamber of the eye, in between the iris and the cornea. Veriseye is made of rigid PMMA plastic. The Ophtec phakic IOL is named "Artiflex™", and it also is implanted in anterior chamber of the eye. It is available as sphere or toric. Phakic IOLs are FDA-approved for refractive correction for people between the ages of 21 and 40 years old, and for refractive errors between −6 D and −20 D.

Phakic IOLs have many advantages. Compared to traditional contact lenses, phakic IOLs are permanently implanted so there is no daily routine of putting them in and taking them out. Compared to LASIK or PRK, phakic IOLs can often be implanted in eyes that are not suitable for LASIK or PRK due to conditions such as thin corneas or extreme myopia that is outside the range that LASIK is able to treat. Sometimes, a phakic IOL can be placed in an eye that has extreme myopia to correct the majority of the refractive error, and then LASIK subsequently corrects the residual error. Phakic IOLs are also used to help with keratoconus and other conditions where the cornea is aberrated. These currently provide a correction for the spherocylinder aberrations, but not higher orders.

The disadvantage of phakic IOLs is that generally the level of visual acuity that is achieved is not as good as what is routinely achieved with ordinary contact lenses or LASIK. According to Dr. Brian Boxer-Wachler, writing on the website AllAboutVision: "In a study of 3-year outcomes of the FDA clinical trial of the Veriseye lens, 84% of patients achieved uncorrected vision of 20/40 or better, which is the legal limit for driving without prescription eyewear in most states. And, 31% achieved uncorrected vision of 20/20 or better. In FDA trials of the posterior chamber Visian ICL, 81% of patients achieved uncorrected visual acuity of 20/40 or better. Forty-one % attained uncorrected vision of 20/20 or better." By comparison, for LASIK, over 90% of patients attain uncorrected vision of 20/20 or better.

Patients that need phakic IOLs generally have more severe visual problems than the typical LASIK patient, who may be only need a few diopters of refractive correction. Also, part of the modem success of LASIK has been the application of wavefront measurement in surgical planning and in post-surgical evaluations that have resulted in steady improvements in the LASIK treatments. Surgeons can target precise treatment zones for LASIK by use of iris registration eye tracking techniques. Wavefront guided techniques have not been used for phakic or pseudophakic IOLs, partly due to the belief that surgeons do not have good control or the ability to predict exactly where an IOL will end up in the eye after it has been implanted.

In addition to phakic IOLs, the pseudophakic IOL replaces the cataractous lens in the eye. For an eye with significant corneal aberrations, replacing the natural lens will not reduce the corneal aberrations. Thus, it may be desirable for some patients to customize a pseudophakic IOL.

The goal of present invention is to use wavefront sensing technology for phakic and pseudophakic IOL planning, implantation, and evaluation steps to improve visual outcomes. Phakic and pseudophakic IOLs present various technical differences and difficulties that require novel ideas to enable effective systems and procedures. These include being able to dynamically measure the eye and predict the final (stable) IOL position. Horizontal (X-axis) and vertical (Y-axis) mis-positioning (mis-alignment) is one area of difficulty. Also, the precise axial location of the IOL along the optical Z-axis of the eye is of concern. Another area of difficulty is that phakic IOLs are frequently used for patients that have keratoconus (progressive thinning of the cornea). Theoretically, a customized IOL can be machined to correct aberrations from the cornea once those aberrations have been measured with a wavefront aberrometer. But the customized shape typically would only achieve 20/20 vision if the phakic IOL were positioned within 0.2 mm of the optical axis and rotated to within 5° of the ideal position. Increased displacements from the ideal position result in a reduction in visual acuity that is progressively more pronounced as the displacement and misalignment increases.

Visian™ phakic ICLs made by Staar Surgical also have a unique feature, which is small, central micro-hole (e.g., U.S. Pat. No. 10,485,655). Early versions of Visian™ ICL's did not have the micro-hole, and some patients developed cataracts in response to the implanted IOL. Initially, the cause was believed to be contact between the crystalline lens and the phakic IOL. However, it was found that a central micro-hole actually prevented cataract formation, probably because it enabled fluid exchange. The micro-hole is small, so it has minimal effect on the visual acuity of the patient. The micro-hole is difficult to see by someone who is looking at the IOL, but it can be detected under slit lamp examination. For adapting wavefront technology to Visian™ ICL lenses, the central micro-hole can serve as a good indicator of phakic IOL's XY-position after implantation. For the Visian™ phakic IOL, positioning within 0.25 mm has routinely been achieved. [Xiaojian He et al, "Relative position of the central hole after EVO-ICL implantation for moderate to high Myopia," BMC Ophthalmology (2020) 20:305]

Wavefront aberrometers have been effectively used to measure the ocular aberrations of the human eye. A small spot of light is projected onto the cornea and the scattered light is collected by the lens and cornea and then imaged onto a wavefront sensor (e.g., Shack-Hartmann, pyramid, interferometer, etc.) [U.S. Pat. No. 5,511,180]. The sensor measures the wavefront of the light rays to determine optical properties of the eye U.S. Pat. No. [6,550,917, RE42,782 D, U.S. Pat. Nos. 7,699,467, 6,848,790, WO 99/27334, WO 00/19885, WO 00/08415, U.S. Pat. Nos. 6,634,750, 5,430, 509, 6,086,204, 6,511,180, 6,095,651, 6,086,204, 5,777, 719]. The measurement can be analyzed in terms of standard Zernike polynomials and provides detailed information about the ocular optical system. Wavefront-based refraction has been shown to closely match the refraction measured with subjective methods [E. Manche, "*Wavefront-optimized versus wavefront-guided LASIK: One-year results of a contralateral eye study*," ASCRS 26 2018]. The traditional refraction is derived primarily from the low-order aberration terms, while higher-order terms describe additional aberrations of the eye. These higher-order aberrations (HOAs) can affect vision quality, as well as the base refraction.

Measured wavefront aberrations have been used as a guide for surgical correction of a patient's vision. Laser refractive surgery has developed systems and methods for using the wavefront information to either optimize optical structures U.S. Pat. No. [7,044,944] or directly guide the surgery U.S. Pat. No. [5,949,521, 6,095,651]. Specialty optical instruments have been developed to incorporate both wavefront aberrometry and corneal topography in a single instrument, which allows for co-aligned measurement of the total aberrations and anterior cornea along a single (and known) optical fixation axis. This provides information needed for guiding the surgery, and for planning a laser treatment that incorporates known reflection and beam footprint calibrations ["*Clinical and patient reported outcomes after wavefront-guided LASIK for myopia using a high definition Hartmann Shack Aberrometer*," C. Kraff, R. Maloney, and S. Coleman, ASCRS 23_2018.]. The wavefront-guided treatment methodology has been shown to be effective at producing excellent patient outcomes using laser refractive surgery [S. Moussa et al, "*Visual, aberrometric, photic phenomena, and patient satisfaction after myopic wavefront-guided LASIK using a high-resolution aberrometer*," Clinical Ophthalmology 2016:10 2849-2496; C. Blanton, "*Meta-analysis of six excimer laser platforms of safety and efficacy in myopic Laser-Assisted in situ keratomileusis*, US Ophthalmic, Review, Vol 8 (1), Spring 2015]. The wavefront-guided approach has also been applied to other treatment modalities U.S. Pat. Nos. [5,777,719, 6,086,204], including contact lenses U.S. Pat. No. [6,499,843, 6,554, 425, 6,830,712, and WO 04072709A], with some success.

Both wavefront-guided and wavefront-optimized methodologies are useful treatment options for many patients. Wavefront-guided (WFG) methods refer to a process where the aberrations of an individual eye are measured and then a customized correction pattern is created for that particular eye. This is also known as wavefront-customized (WFC). Wavefront-optimized methods refer to a process where a large number of eyes have been measured and a correction pattern is determined that is the best correction to apply to an average eye. Historically, wavefront-optimized was developed to correct a previously unknown problem. LASIK was developed before wavefront measurements became common. When wavefront measurements were done on eyes that had been treated with LASIK, it was discovered that conventional LASIK was causing spherical aberration. The reason was the more a surface is sloped, like at the edge of the curved surface (cornea), the more laser power needs to be applied to create the desired surface via ablation. This fact had not been fully understood during the early development of LASIK. The primary benefit of "wavefront optimized" was that it incorporated this new knowledge into the laser treatment pattern so that it did not introduce the unintended spherical aberration. Wavefront-optimized is targeted to an average eye, and when averaging over many eyes, the high-order aberrations like coma and trefoil are nearly zero. Thus, wavefront-optimization has little effect on reducing high-order aberrations for an individual eye.

The phrase "wavefront-optimized" can be somewhat confusing to patients. It implies that it is a form of wavefront-guided LASIK; but it is not. Wavefront-optimized LASIK is in many ways simply conventional laser surgery, but with modifications based on wavefront modeling and wavefront theory to improve outcomes beyond conventional LASIK. With wavefront-optimized LASIK, a refraction is still performed on the patient to generate a prescription to be entered into the laser, as is the case with standard conventional surgery. However, standard conventional laser surgery has been shown to increase a type of higher order optical aberration in the eye called "spherical aberration". To counteract this optical error in conventional surgery, a pre-set number of laser pulses are applied to the periphery of the laser ablation zone to negate the spherical aberration otherwise induced by conventional laser surgery. In this way, "wavefront-optimized" surgery simply is an improved version of conventional laser surgery.

True wavefront-guided LASIK, by contrast, targets an elimination of all higher order aberrations, rather than simply targeting a lack of increase in spherical aberration. Wavefront-guided LASIK aims to fully correct the optical fingerprint; which is the complete and complex measurement of all the higher order aberrations including, but not limited to, spherical aberration. Wavefront-guided LASIK, unlike wavefront-optimized LASIK, therefore, is not designed simply just to avoid an increase in one specific higher order aberration (spherical aberration); rather, it is designed actually to address all higher-order aberrations, including spherical aberration. As expected, conventional LASIK surgery increases higher-order aberrations, and wavefront-optimized LASIK surgery induces fewer higher-order aberrations, but wavefront-guided LASIK surgery resulted in even fewer higher-order aberrations.

Some other technologies exist that provide correction for optical error of the eye. The World Health Organization estimates that 20 million IOLs were implanted worldwide in 2010, and they project 32 million will be implanted annually by 2020. The vast majority of IOLs are simple monofocal designs, but increasingly "premium" (wavefront-optimized) IOLs are being developed that incorporate wavefront adjustments into their design. The IOL may be implanted in the capsular bag after removal of the natural (presumably cataractous) lens, or implanted in the sulcus, just behind the iris U.S. Pat. No. [10,485,655], or even "clipped" to the iris itself.

Newly developed techniques can modify the refractive/diffractive characteristics of an IOL or ICL in-vivo by changing the index of refraction, n, with a small spot, scanning, low-energy, pulsed femtosecond (FS) laser beam operating at a very high repetition rate [L. Zheleznyak, "*First demonstration of human visual performance through refractive-index modified ophthalmic devices written in hydrogels*," IOVS Vol. 58(8) 1274-1274; G. Gandara-Montano, "*Optical bench testing of gradient-index Fresnel lenses written with femtosecondlaser induced refractive index change*," IOVS Vol. 58(8), 1275-1275]. See also US patents: [2008/0001320, 2019/0343683, U.S. Pat. Nos. 8,512,320, 9,107,746, 8,292,952, 9,192,292]. Changes in the IOL's index of refraction of up to +0.06 (~4% change from n=1.5) can be achieved before any ablation of tissue occurs. A change of 0.01 in the index of refraction of an ocular structure (cornea, IOL) can result in a magnification change of 3 Diopters. Some of these processes apply multiple femtosecond laser pulses to the cornea to "write" a buried layer (index modified zone) inside the cornea that has the altered index of refraction. A related process locally changes the IOL's polymer properties from hydrophilic to hydrophobic (or visa-versa) by using the FS laser.

Another similar process that uses the FS laser beam is called "LIRIC", which stands for Laser Induced Refractive Index Change. Using LIRIC, implanted IOL's have been corrected in-situ for base diopter and asphericity parameters, but not for HOA's. The beam in the eye must be precisely positioned and controlled, which requires accurate measurement to direct and monitor beam delivery. The process of writing a desired optical pattern on an IOL can take tens of seconds. During that time, the IOL may move in the eye, even if the eye has been fixed by external means. A method is needed to accurately track the XYZ position and tip/tilt of the IOL in the eye in real-time during the FS laser surgical procedure. The use of a FS laser to change the properties of an implanted IOL is not yet FDA approved, although human trials are underway.

A number of optical techniques have been developed to measure structures in the eye, including wavefront aberrometry, corneal topography, ultrasound, and ocular coherence tomography (OCT). However, these techniques are usually aimed at a more general diagnosis of the eye, and they lack the combination of accuracy, dynamic range, and speed to actively control surgical procedures. More simple optical techniques that provide location (XYZ) and tip, tilt and rotation of an object can have a wide range and operate fast enough to control a surgical procedure in real time.

Measurement of a patient's wavefront pattern with a wavefront aberrometer, that is made before a surgery, can be used to make an ideal wavefront-customized IOL. The design of the IOL must take into account where the IOL will be located in the eye. It is obvious that the wavefront pattern must match in the XY location. The Z location also is important because there is a magnification effect that depends on the axial distance between the IOL and the cornea. When the wavefront of the eye is measured, the light rays exiting the cornea create an apparent diameter called the "exit pupil" defined by the physical iris in the eye. The actual physical iris is smaller than how it appears from the outside because of the magnification effect of the cornea. Consequently, the externally measured wavefront of pattern has to be scaled down in size on the IOL that will be implanted in the eye, and the scaling factor depends on the radius of curvature of the cornea and the axial distance the IOL has to the cornea. Note: more accurate scaling and distortion factors can be accomplished by using raytracing techniques.

BRIEF SUMMARY OF THE INVENTION

A method and system for correcting vision in an eye that uses a 3-D wavefront-customized phakic or pseudophakic Intraocular Lens (IOL), the method comprising: (1) measuring wavefront aberrations of the eye; (2) designing a wavefront-customized correction profile for an IOL, taking into account the location that the IOL; (3) fabricating an IOL using the customized correction profile; and (4) implanting the customized IOL in the eye, without having to remove the natural lens in the case of a phakic IOL. Alternatively, an uncorrected IOL is first implanted the eye, followed by scanning a femtosecond laser spot across the implanted IOL to locally change the Index of Refraction of the IOL material and create an in-situ wavefront-customized IOL. This latter method can be used for both phakic and a pseudophakic IOLs.

DETAILED DESCRIPTION OF THE INVENTION

Figure 1:
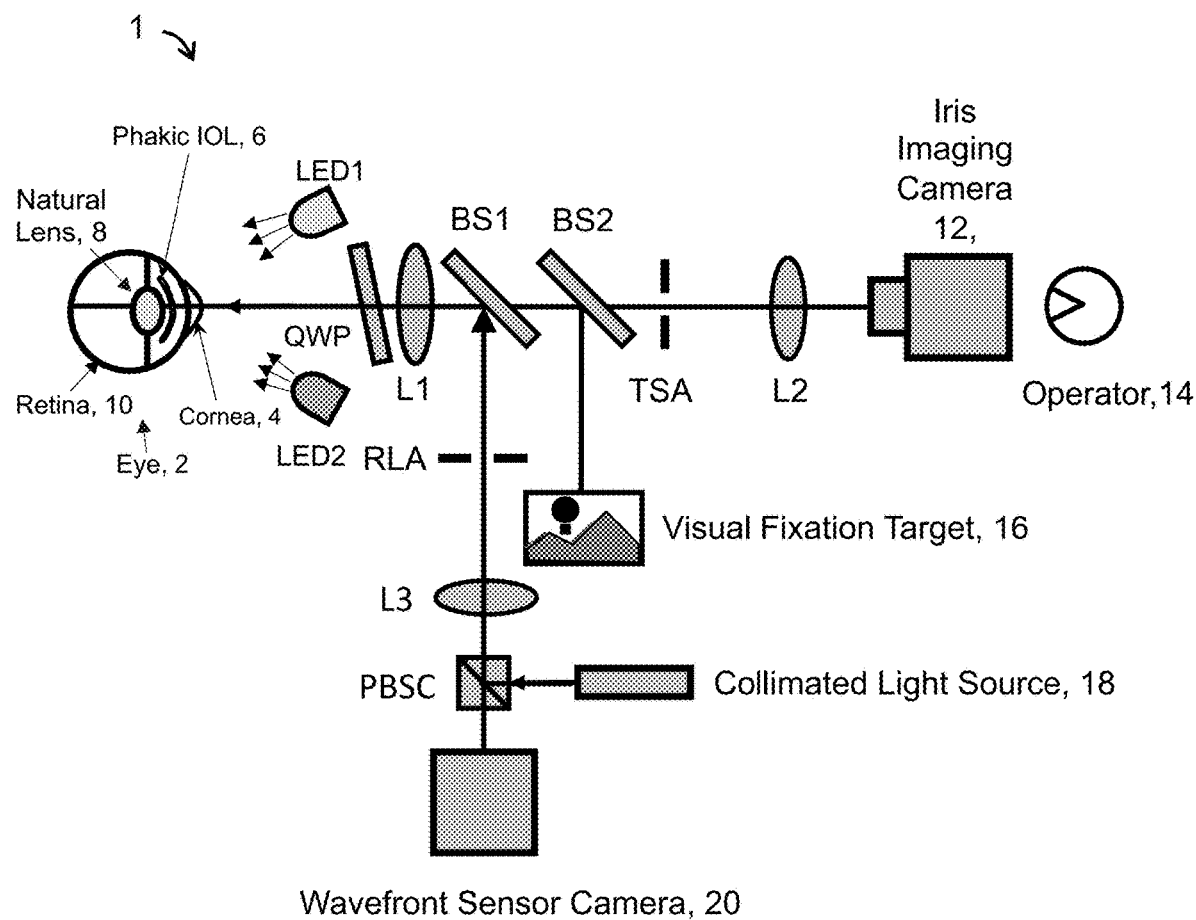
FIG. 1 shows a schematic optical layout of a first example of an ophthalmic wavefront aberrometer, according to the present invention.

The invention described herein relates to both instruments and processes for using the instruments to guide the manufacture and use of Intraocular lenses (IOL) for improving vision. Note: the phrase "conventional 10" refers to an IOL that is un-corrected with respect to higher-order aberrations (HOAs). In other words, a conventional IOL corrects for low-order aberrations (defocus and astigmatism), but not for higher-order aberrations. The present invention covers both phakic IOLs and pseudophakic IOLs, depending on whether the natural crystalline lens is present or has been removed, respectively. Hence, the term "IOL" broadly includes phakic and pseudophakic IOLs.

The following acronyms are used herein: WF=WaveFront; WFD=WaveFront Dynamics; WFG=Wavefront Guided; WFE=Wavefront Error; WFS=WaveFront Sensor; LOA=Lower Order Aberration, HOA=Higher Order Aberration, RMS=Root Mean Square; IOL=Intraocular lens; CIOL=Customized IOL; SCA=Sphere, Cylinder, and Axis; Pt=patient, SLD=Super Luminescent Diode, $S_{eq}$=Spherical Equivalent; BS=Beam Splitter; RLA=Range Limiting Aperture; TSA=Telecentric Stop Aperture, OD=right eye; OS=left eye; DTF=Dynamic Tear Film, HORMS=Higher Order RMS, ECP=Eye Care Practitioner; and OCT=Optical Coherence Tomography. The phrase "3-D IOL" refers to a non-axisymmetric IOL that is not rotationally asymmetric. The adjectives "wavefront-guided" and "wavefront-customized" mean the same thing. The phrase "3-D customized IOL" means that the IOL is non-axisymmetric (rotationally asymmetric). All references cited herein are incorporated by reference in their entirety.

The words "accommodate" and "accommodative" both refer to the condition where the eye automatically adjusts the shape of its natural (biological) crystalline lens to re-focus the eye when the gaze target distance changes. Typically, "accommodation" results in an increase in optical power and a reduction in pupil size. The words "sequential" and "sequence" refers to a dynamic, time-dependent set or series of measurements. The phrases: "alignment camera", "iris imaging camera" and "eye imaging camera" mean the same thing. The word "aberrometer" refers to a multi-use optical instrument that is broadly construed to include both refractometer and autorefractor systems. Finally, HOA's can be described by a standardized set of 10-20 Zernike polynomial coefficients, or by a wavefront error surface.

This application is related to 3 co-pending non-provisional US patent applications by Daniel R. Neal, et. al: Ser. No. 17/175,335 filed Jan. 9, 2021; Ser. No. 17/180,838 filed Feb. 21, 2021; and Ser. No. 17/183,327 filed Feb. 23, 2021; wherein all three of these applications are included herein by reference in their entirety.

In order to measure the wavefront aberrations of the eye with sufficient accuracy and dynamic range, a high-dynamic range aberrometer system must be used. Wavefront aberrations can be measured with a Hartmann-Shack sensor, scanning deflectometer, pyramid sensor, sciascopy, or other methods. However, with modem high resolution, high speed cameras, it is possible to design systems with sufficient accuracy and dynamic range to measure most eyes. For a Hartmann-Shack sensor, the techniques of U.S. Pat. No. 6,550,917 can be effectively applied herein, using a Range Limiting Aperture (RLA) to limit crosstalk between adjacent lenslet channels inside the wavefront sensor.

In order to sample the optics of the eye, a small spot of light is projected onto the retina by a probe beam. This light source can be a laser, Super-Luminescent Diode (SLD), LED, or other relatively-low intensity light source. Advantageously, a fiber-coupled, infrared SLD can be used to provide a good quality beam that can be imaged onto the retina, with the iris imaging camera being sensitive to infrared light. The use of a fiber-coupling component provides opportunities to splice multiple fibers with different sources at different wavelengths. This can provide additional information useful for imaging multifocal optics (i.e., multifocal contact lenses).

FIG. 1 is a schematic optical layout of a first example of a basic ophthalmic wavefront aberrometer, according to the present invention. The first step of using this instrument is that the instrument operator 14 aligns the instrument 1 to the patient's eye 2 along the main optical axis of the instrument 1. The operator 14 is aided in this task by viewing an image of the ins that is displayed by the on-axis iris imaging camera 12. Once the eye is illuminated using illumination sources LED1 and/or LED2, and the instrument is properly aligned by the operator 14, the patient is instructed to look at the internal visual fixation target 16. Target 16 typically simulates a distant landscape scene; for example, a hot air balloon hovering over a distant horizon. The fixation target 16 itself is preferably a micro-video-display that can be programmed with different targets and illumination levels.

This can be used to project eye charts, individual letters, geometric patterns, and scene targets. It is even possible to project short movie loops or GIFs.

Continuing with FIG. 1, while the patient looks at the fixation target 16, the Collimated Light Source 18 emits a narrow beam of light. The light in the collimated beam can be S-polarized, and it is barely noticed by the patient because, preferably, source 18 can be a Super-Luminescent Diode (SLD) emitting non-visable infrared light with a wavelength of 840 nm. Other wavelengths can be used, as needed. The light reflects off the hypoteneuse in the Polarizing Beam Splitting Cube (PBSC). The light travels through lens L3, through Range Limiting Aperture (RLA), reflects off a first beam splitter, BS1, travels through lens L1, and then through a quarter wave plate (QWP). The QWP converts the light to circular polarization. The light then travels into the eye as a narrow, collimated beam of polarized light. The cornea 4 and natural lens 8 focus the beam onto the retina 10 at the back of the eye. 2 A small fraction of the light then scatters off the retina in all directions. About one-half of a percent of that light then goes back toward the cornea and creates an outgoing beam from the eye that is same diameter as the iris. For an emmetrope, the outgoing beam is nearly collimated with parallel rays. For a myope, the beam converges slightly as it leaves the cornea. Conversely, for a hyperope, the beam diverges slightly. The light beam then passes through the QWP and is converted to P-polarization. The light travels through front lens L1, reflects off BS1, passes through lens L3 and then reaches the PBSC. Since the light beam has been converted to P-polarization, it passes through the PBSC, wherein it then reaches the wavefront sensor camera 20. A micro-processor (not shown) analyzes the images captured by the wavefront sensor camera and then calculates the patient's base refraction and higher-order aberrations (e.g., in terms of standardized Zernike polynomial coefficients).

Figure 2:
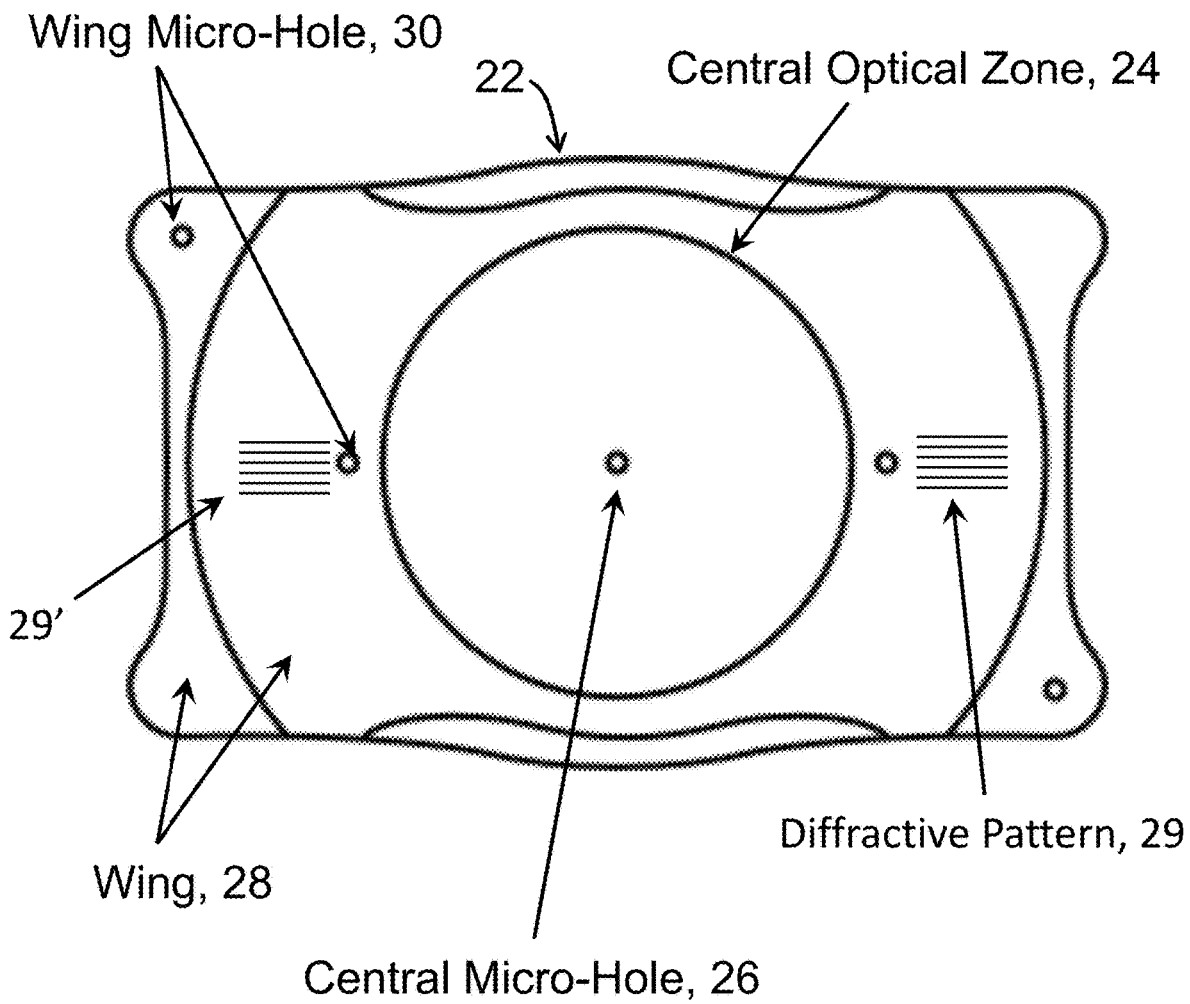
FIG. 2 shows a plan view of an example of a "Visian™ ICL" (phakic IOL) that has a central micro-hole disposed in the center of the IOL.

FIG. 2 shows a plan view of an example of a "Visian™ ICL" (phakic IOL 22) that has a small, micro-hole disposed 26 in the center of the IOL. The micro-hole allows fluid exchange across the IOL's structure, which prevents the IOL from inducing cataract formation. The larger circle 24 represents the outer circumference of the central optical zone 24 of the IOL. The rectangular portions are the haptic wings 28 that fit into the space in between the iris and the natural lens of the eye and hold the lens securely in place (i.e., in the posterior chamber). See, also, FIG. 3. Additional thru-holes can be added (e.g., additional micro-holes 30, or short lines/scratches on the surface) to further mark the IOL with one or more fiducial marks (up to a point where visual acuity is affected). Fiducial marks on a phakic IOL are automatically located using image processing software. One embodiment of the aberrometer instrument could measure the wavefront of the eye and nearly simultaneously find the XY-position of the ICL using its central hole as a fiducial mark (i.e., landmark) and the iris imaging camera. Another option is to use a femtosecond laser to create fiducial marks on the phakic IOL that can be used for guiding the motion of a following laser pulse. Such fiducial marks can be either simple spots that scatter light coherently, or deeper pits that scatter light incoherently. Or, they can be created to have diffractive properties, such as uniformly-spaced holes or lines 29, 29' (e.g., a diffraction grating) that scatter light preferentially more strongly at certain incident angles and color combinations. Such a diffractively-coded system can be created so a color camera effectively "sees" distance as color variations across an image.

Figure 3:
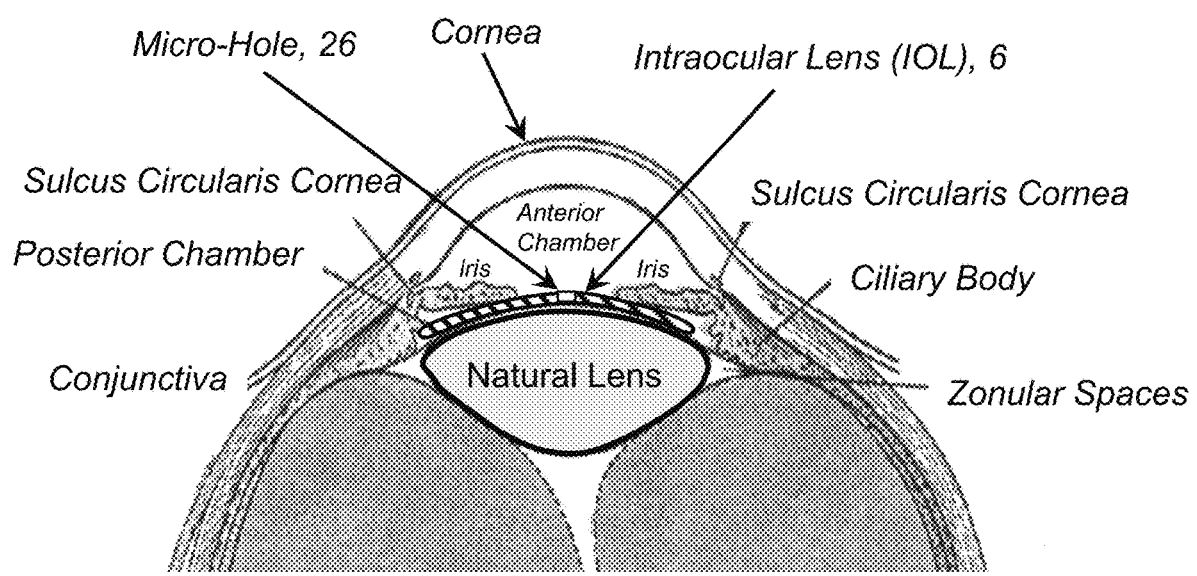
FIG. 3 shows a cross-section view of an example of the geometry of a normal phakic human eye with an implanted phakic IOL, with the natural crystalline lens still in place.

FIG. 3 shows a cross-section view of an example of the geometry of a normal phakic human eye with an implanted phakic IOL 6, and with the natural crystalline lens still in place. The phakic IOL is usually implanted just behind the iris in the Posterior Chamber, and is constrained by the ciliary body and the natural lens. Alternatively, (not shown) it can sit in-between the cornea and iris in the Anterior Chamber.

Figure 4A:
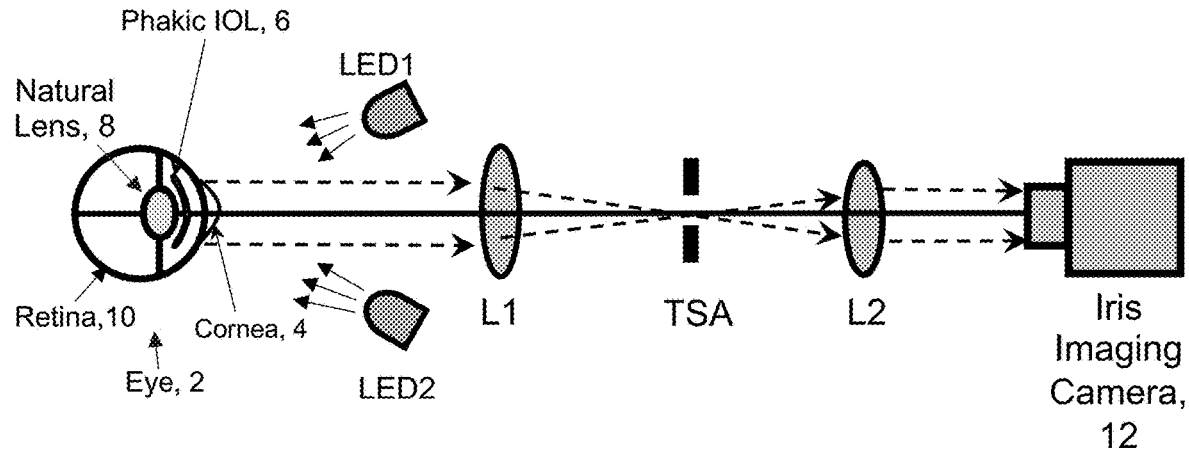
FIG. 4A is a schematic optical layout of an optical system for imaging the anterior segment of an eye showing the central rays, according to the present invention.
Figure 4B:
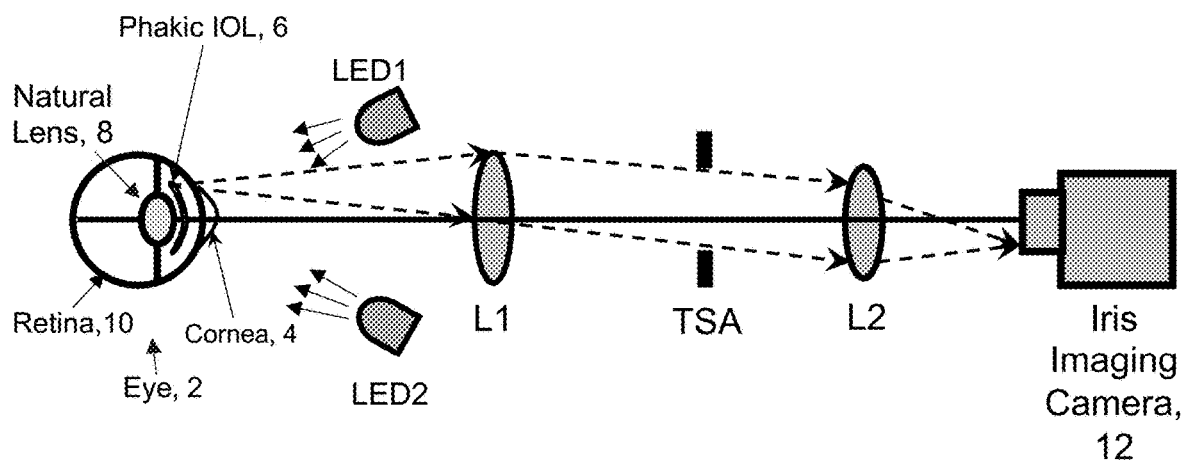
FIG. 4B shows a schematic optical of an optical system for imaging the anterior segment of an eye showing an off-axis set of rays, according to the present invention.

FIGS. 4A and 4B show a schematic optical layout of a second example of an ophthalmic iris imaging system, according to the present invention. This example shows a regular Ins Imaging System. The arrangement comprises a front lens, L1, and rear lens, L2, which are configured as a telecentric teleobjective (where Lenses L1 and L2 are separated by a distance that equals the sum of their focal lengths). An light-restricting aperture, labeled "TSA" (Telecentric Stop Aperture), is placed in-between lenses L1 and L2. The TSA stop is located one focal length, f, away from both lenses. This is a conventional setup, and the image of the eye that forms on the camera is a normal one. The TSA can simply be a hole of about 3 mm diameter in a solid (opaque) disc. The TSA serves as a restriction that allows only rays to reach the iris camera if they enter the instrument traveling nearly parallel to the optical axis of the instrument, as illustrated by the dashed lines in FIG. 4A.

FIG. 4B shows a pair of off-axis light rays emitted from an upper edge of the phakic IOL 6, which focus on the iris imaging camera 12 at the far end of the device. Notice that the opening (aperture) in the telecentric stop (TSA) can be enlarged as needed to accommodate these off-axis ray traces.

Figure 5A:
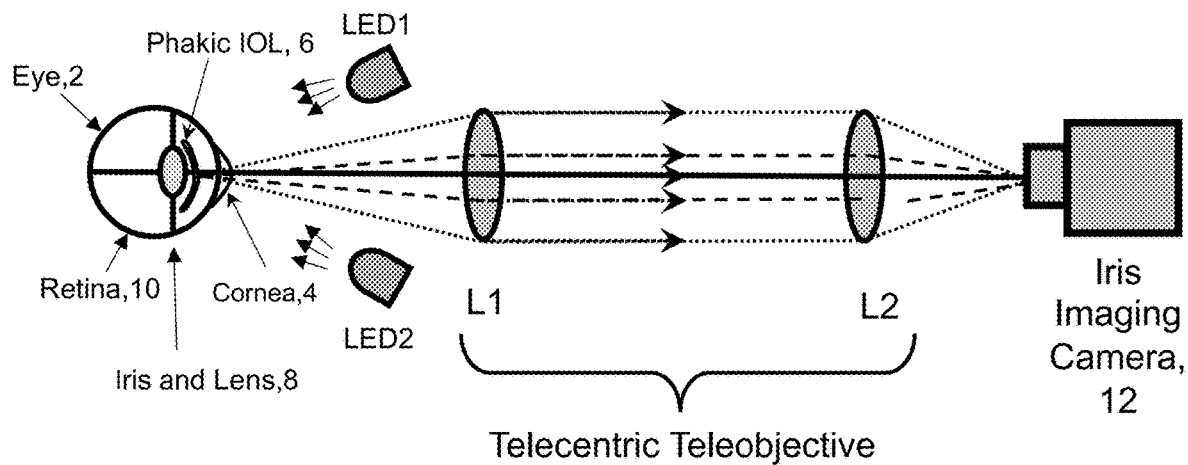
FIG. 5A is a schematic optical layout of a optical system for imaging the anterior segment of the eye with no dark field illumination system, according to the present invention.

FIG. 5A is a schematic optical layout of an example of an a conventional iris imaging system, according to the present invention. This figure illustrates light rays emitted by the central micro-hole of phakic IOL 6. The central telescope region located in-between front lens L1 and rear lens L2 forms a telecentric teleobjective, within which the light rays are aligned parallel to the main optical axis. Here, we also see that the optical plane of the phakic IOL 6 is optically conjugated to the optical plane of the iris imaging camera, 12. No telecentric stop aperture is shown in this figure for comparison.

Figure 5B:
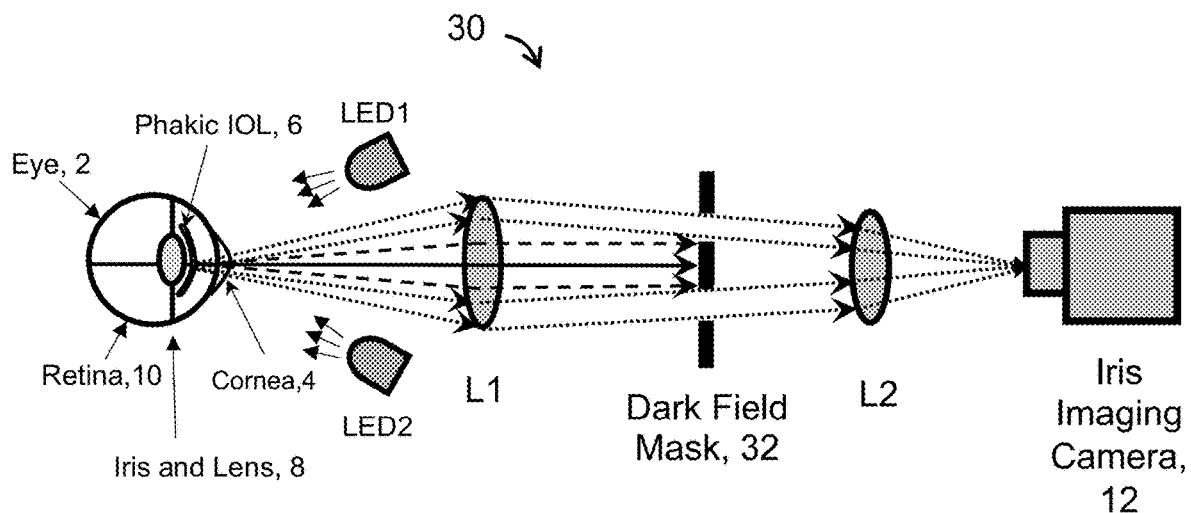
FIG. 5B is a schematic optical layout of an optical system for imaging the anterior segment of an eye with a dark field mask to block undeviated light, according to the present invention.

FIG. 5B is a schematic optical layout of a dark-field iris imaging system 30, according to the present invention. This is the same optical layout as shown in FIGS. 4A and 4B, except that the TSA optical component is now replaced by a Dark Field Mask 32 (DFM) optical component that has a central obscuration (opaque central disk). Dark field imaging is a well-known technology to those skilled in the art of optical imaging. However, its use for imaging eye structures and features of optical structures implanted in eyes is novel. The rounded edge of micro-holes 26 and 30, and diffraction grating 29, in/on the Visian™ phakic IOL 6 (see FIG. 2) will tend to scatter light in many directions that are not parallel to the instrument's main optical axis. Hence, the dark field mask 32 is useful to preferentially image the edges of objects, particularly if they have been illuminated by off-axis light from LED1 and/or LED2 coming in from the side. Note that in FIG. 5B the central light rays are blocked by the central obscuration of the Dark Field Mask 32. The off-axis light rays emitted by the phakic IOL 6 are focused by lens1 and lens 2 onto the iris imaging camera 12.

Figure 5C:
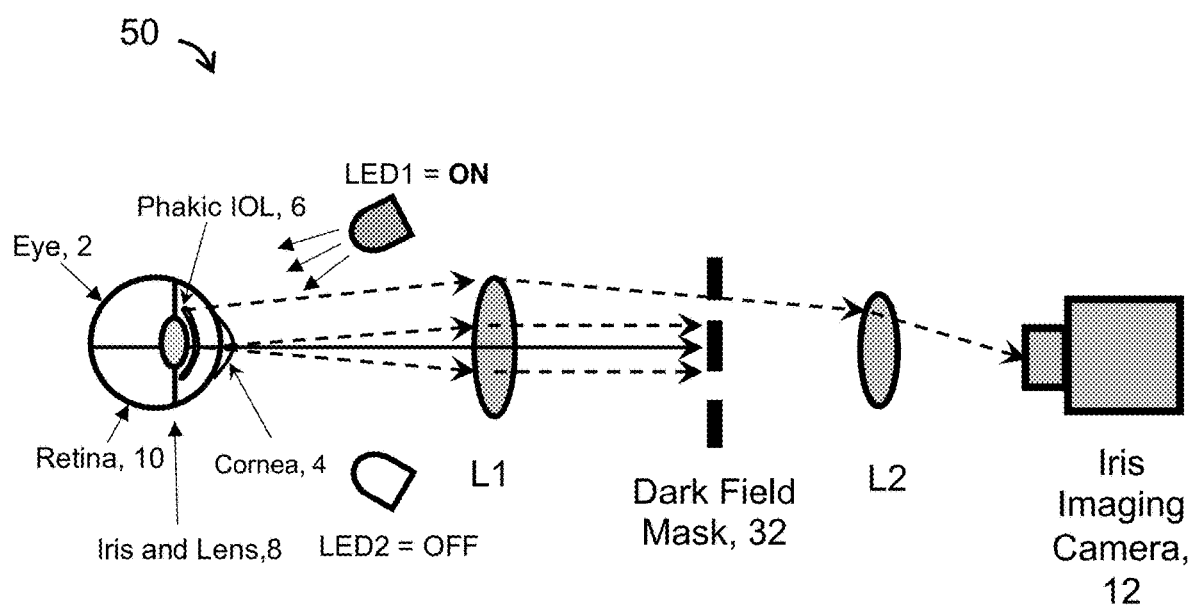
FIG. 5C is a schematic optical layout an optical system to image the anterior segment of an eye showing unblocked deviated rays and blocked undeviated rays, according to the present invention.

FIG. 5C shows another schematic optical layout of a dark-field imaging system, according to the present invention. This is the imaging portion of the aberrometer system of FIG. 1 and is modified by using a pair of individually controllable, off-axis illumination sources (e.g., LED1, LED2) emitting light at the same wavelength; or, at two measurably-different wavelengths (Lamda1, Lamba2). By switching the upper side of the illumination sources ON (e.g., LED1=ON and LED2=OFF), only one side of a fiducial mark, or the edge of the haptic wings, on the IOL 6 would be illuminated. This will have the effect of greatly enhancing the shadows to make the edges and fiducial feature(s) more evident. Optionally, the LEDs could be alternatively switched ON/OFF on alternate frames of the iris camera using software control means. This system can optionally alternate between using two different illumination wavelengths (Lamda1, Lamba2). When Illuminator #1 is ON and Illuminator #2 is OFF, shadows are formed on the right edge of the IOL. When Illuminator #1 is OFF and Illuminator #2 is ON, shadows are formed on the left edge. Thus in successive frames both edges can be identified. Image subtraction is an effective means to find the edges. Structures that are relatively flat will appear similar with the left and right illuminated images. So when images are subtracted, the flat regions will be suppressed. Edges will appear different in the left and right illuminated images, so image subtraction will make those regions stand out.

Other embodiments of an aberrometer, according to the present invention, could physically switch between the two different configurations shown in FIGS. 4A, 4B and 5B by:
(1) using a solenoid (not shown) to physically exchange the two items (TSA and DFM) on the main optical path, or
(2) using a small stepper motor and rotation disk (not shown) with different apertures or obstructions disposed thereon, or
(3) other modulation means (not shown) for repeatedly modulating the light travelling along the main optical path.

Figure 6:
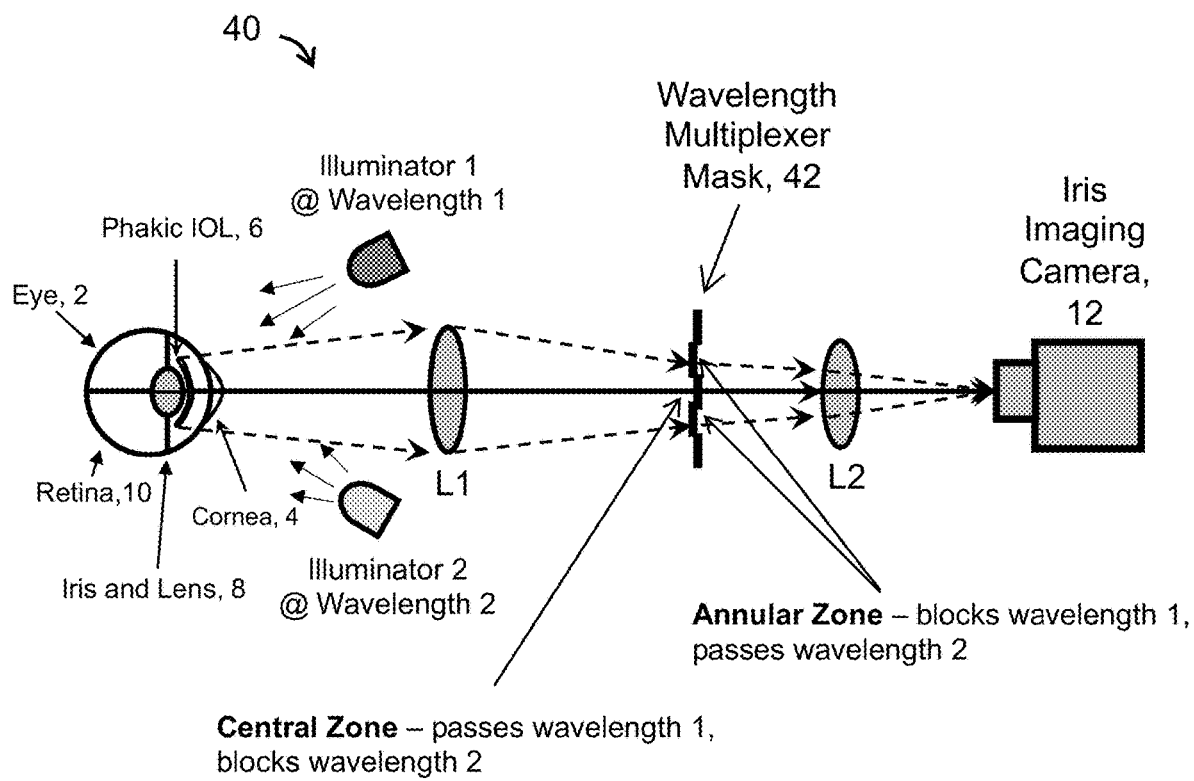
FIG. 6 is a schematic optical layout of an optical system for imaging the anterior segment of an eye with a wavelength multiplexing scheme to successively pass/block different color light, according to the present invention.

FIG. 6 shows a schematic optical layout of a third example of the imaging portion of an ophthalmic wavefront aberrometer, according to the present invention. In this embodiment, instead of physically moving/replacing a TSA with a DFM, it is possible to use a stationary, switchable Wavelength Multiplexed Mask (WMM) optical component in place of either of those two components (TSA or DFM). FIG. 6 illustrates an example of such a Switchable WMM Imager system 40. In this embodiment, illuminator LED1 emits light at wavelength #1, while illuminator LED2 emits light at a different wavelength #2. The wavelength multiplexed mask (WMM) can have a central zone that passes wavelength #1 and blocks wavelength #2, while being surrounded radially by an annular region that blocks wavelength #1 and passes wavelength #2. In this system 40, one would get a regular image at the iris imaging camera in both illumination setups. However one would like to have the edges enhanced in some situations. A software subtraction of two sequential images, for example, would make a single dark field image that greatly enhances edge detection of the IOL and of fiducial mark(s) disposed thereon.

The rounded edge of the micro-hole in the phakic IOL will tend to scatter light in many directions not parallel to the instrument's main optical axis. An improved instrument can be constructed so a small motor switches optical component between a TSA telecentric stop and a DFM dark field mask. That would enable a multi-functional, combined instrument that: (1) serves as a corneal topographer, (2) serves as an imager that collect regular iris images, and (3) serves as means to locate the central micro-hole or other fiducial marks in an IOL.

Figure 7:
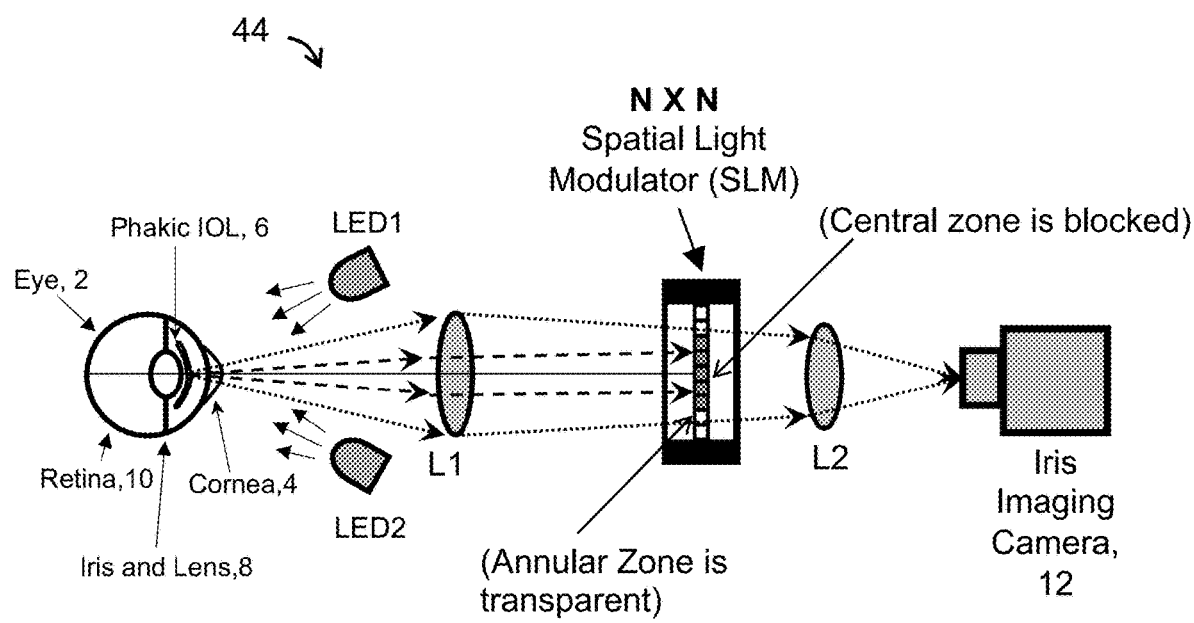
FIG. 7 is a schematic optical layout of an optical system to image the anterior segment of an eye with a spatial light modulator used to selectively enhance certain features, according to the present invention.

FIG. 7 shows a schematic optical layout of a fourth embodiment of the imaging portion of an aberrometer 44, according to the present invention. Instead of physically switching between different physical stops (TSA or DFM), an alternative system comprises a spatial light modulator (SLM) optical component at the location of the previous telecentric stop (TSA). For instance, the SLM can have a grid of N×N hexagonal or square regions (addressable liquid-crystal regions) that can individually and rapidly be turned ON/OFF in transmission mode, thereby enabling a wide variety of edge detection and optical processing techniques (such as mimicking a dark field mask). In one embodiment, N=32.

Recently, femtosecond (FS) lasers have been developed that can change the index of refraction of plastic materials by focusing pulsed FS laser energy onto a small local area and then repeatedly scanning adjacent spots on the plastic to change the optical properties. Such FS lasers can be used to modify the wavefront of IOLs after being implanted (in vivo). Guidance for actively controlling the FS laser spot can be provided by making measurements of the eye's wavefront. It is also necessary to know the XYZ location of the phakic IOL. The existing micro-hole in the Visian ICL™ provides a central marker that can be used as an alignment reference. Alternatively, other fiducial location feature(s), including additional holes or diffractive scratches/lines, can be added to any IOL to enable the use of this optical enhancement technique. Purkinje reflections can be used to determine the tip/tilt angles of the IOL relative to the iris or other feature. The use of sequenced (synchronized) illumination light sources (synchronized with the CCD global shutter cameras) can help with Purkinje image disambiguation.

Convenient methods of locating the XYZ location of the micro-hole (or other fiducial location feature) in an IOL can include using:
(a) split-prism range finders (such as are used in SLR cameras),
(b) OCT systems,
(c) stereo cameras setup, and
(d) bi-cell detectors, or numerous other methodologies.

In some cases, an eye care practitioner will implant a phakic IOL that has toric marks to guide implantation relative to the astigmatism in a patient's eye. Such marks can also be used with a system that delivers a customized wavefront pattern to a phakic IOL via a scanning femtosecond laser.

Typically, the manufacturer has a process for machining their phakic IOLs that can control the amount of base sphere and cylinder refractive errors, as well as creating any desired 3-D wavefront correction pattern or topography for HOAs. Measurement of a patient's wavefront pattern that is made before a surgery can be used to make a wavefront-customized IOL. Based on the results from He (2020 paper), the IOL's position error is less than 0.25 mm. This is sufficient for accurate correction of higher-order aberrations through the $4^{th}$ order.

The outer haptic parts of the phakic IOL (i.e., the "wings") generally extend over to the ciliary body that suspends the lens in the eye. The size and shape of the interstitial space in the Posterior Chamber between the ins and the ciliary body determine the final axial position of the phakic IOL. Currently no clinically reliable means have been found to measure and characterize these interstitial spaces before the implantation of the ICL. Techniques that are being considered include: (a) using long wavelength Ocular Coherence Tomography (OCT) through the ins, and (b) using long wavelength OCT through the sclera. Other techniques can utilize ultrasound and Magnetic Resonance Imaging (MRI) machines. The same techniques potentially can be used with implanted IOLs to learn more about the mechanism(s) that determine where an IOL ends up.

Another area that could use improvement with the current IOLs is that visual acuities reach 20/20 in only about 50% of procedures. This seems to be slightly lower than is achieved with typical monofocal IOL surgeries. Application of customized wavefront techniques would likely result in IOLs achieving better vision outcomes than typical IOL surgeries.

Figure 8:
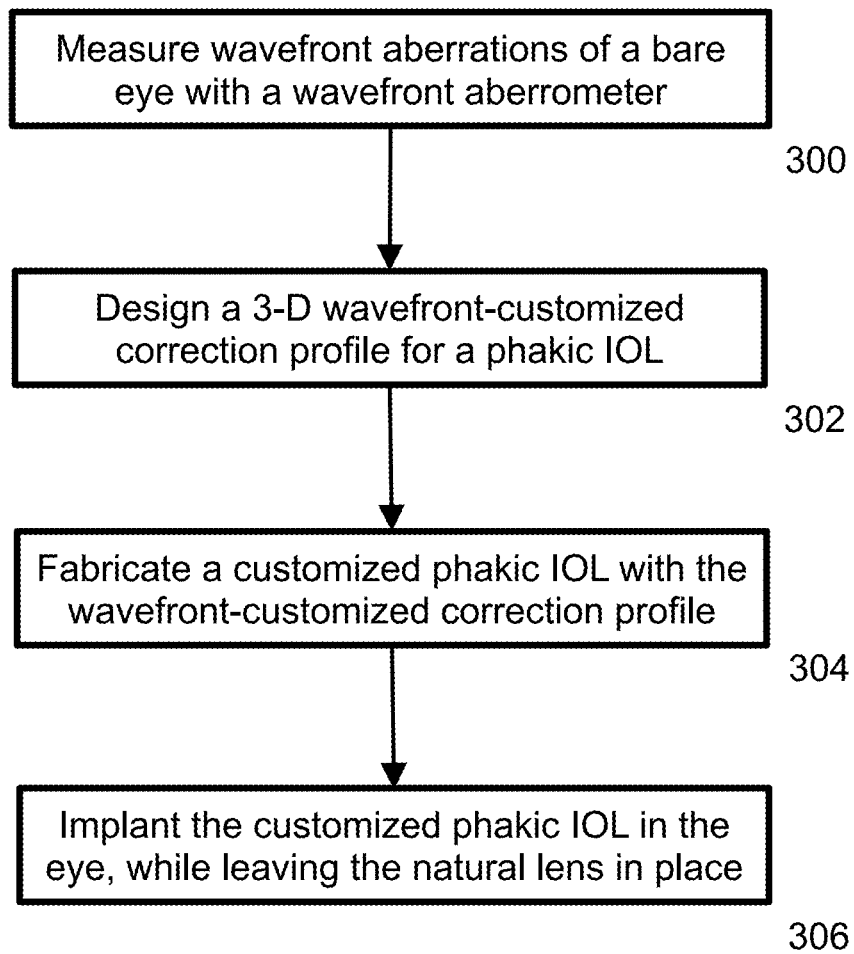
FIG. 8 shows a flow chart illustrating a first example of a method for correcting vision in an eye using a wavefront-customized IOL, according to the present invention.

To design and fabricate a customized phakic or pseudophakic IOL to correct for visual disturbances caused by higher order aberrations, there are a number of process steps that can be performed. FIG. 8 shows a process flow chart illustrating a first example of a method for correcting vision in an eye using a wavefront-customized IOL, according to the present invention. The method comprises:

(Step 300) Measuring one or more wavefront aberrations of a bare eye with a wavefront aberrometer;
(Step 302) Designing a 3-D wavefront-customized correction profile for an Intraocular Lens (IOL);
(Step 304) Fabricating a customized IOL with the 3-D wavefront-customized correction profile; and
(Step 306) Implanting the 3-D wavefront-customized IOL in the eye, while leaving the natural lens in place.

This method is appropriate for phakic IOLs, since the total aberrations of the eye, including cornea and lens, are measured with the first step. Thus, the IOL is the full correction for total aberrations, both high- and low-order.

Figure 9:
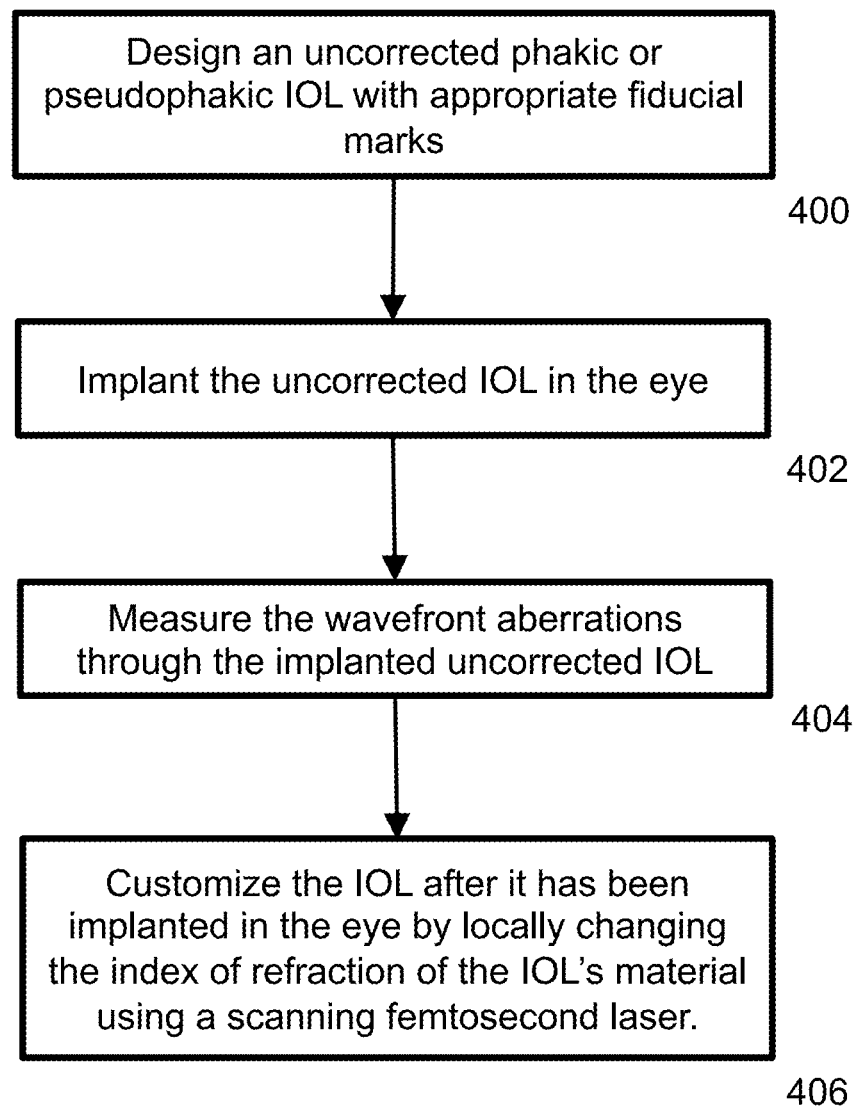
FIG. 9 shows a flow chart illustrating a second example of a method for correcting vision in an eye using a wavefront-customized IOL, according to the present invention.

FIG. 9 shows a flow chart illustrating a second example of a method for correcting vision in an eye using a customized phakic or pseudophakic IOL, according to the present invention. This method comprises:

(step 400) Designing an uncorrected monofocal or toric IOL (that has the appropriate defocus and astigmatism correction, but also includes fiducial marks);
(step 402) Implanting the uncorrected IOL in the eye;
(step 404) Measuring the wavefront aberrations through the uncorrected IOL; and
(step 406) Customizing the IOL after it has been implanted in the eye by locally changing an index of refraction of the IOL's material using a scanning femtosecond laser.

Figure 10:
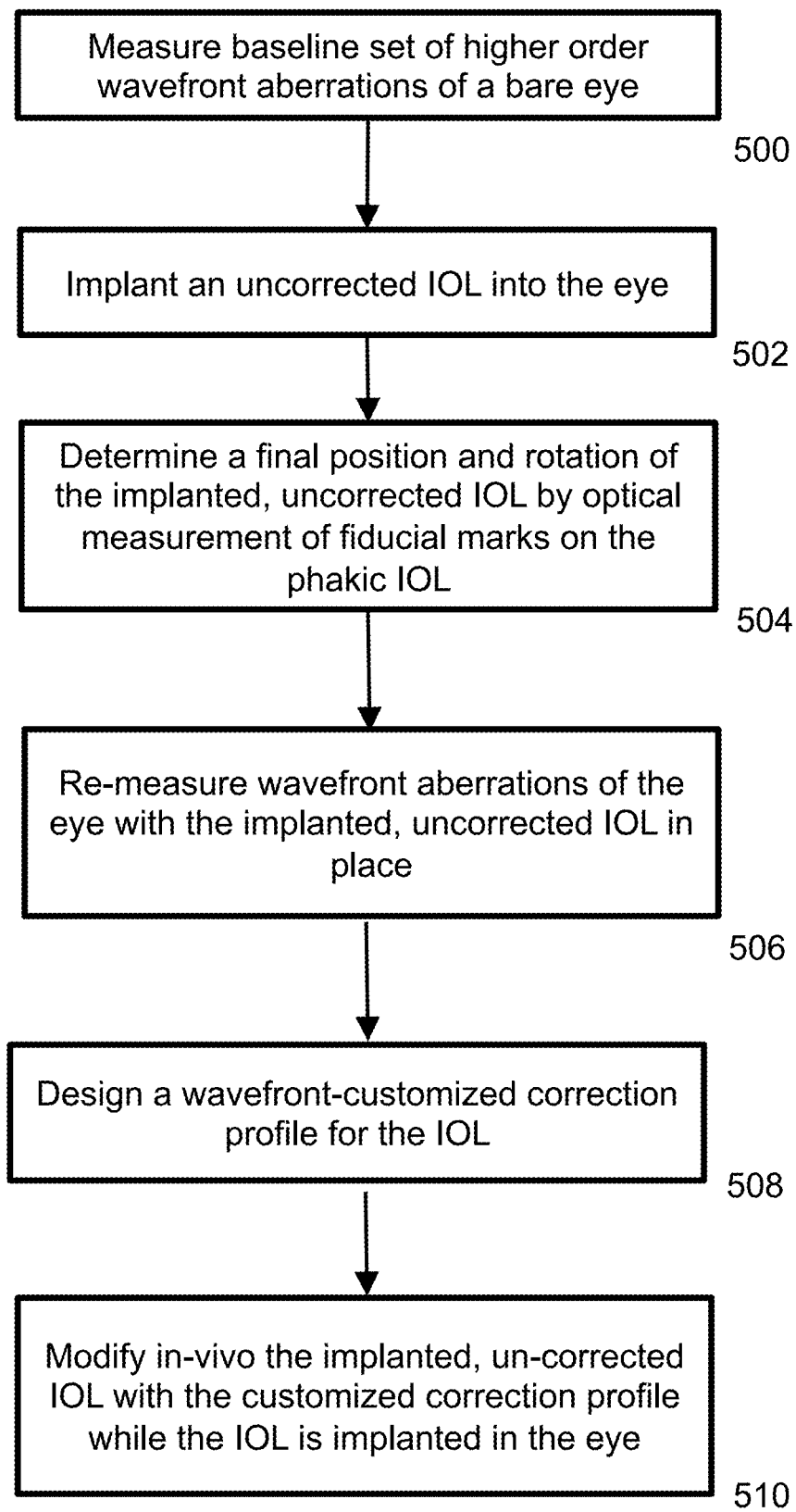
FIG. 10 shows a flow chart illustrating a third example of a method for correcting vision in an eye using a wavefront-customized IOL, according to the present invention.

FIG. 10 shows a flow chart illustrating a third example of a method for correcting vision in an eye using a customized IOL, according to the present invention. This method comprises:

(step 500) Measuring a baseline set of higher-order aberrations of a bare eye with a wavefront sensor;
(step 502) Implanting an uncorrected IOL into the eye;
(step 504) Determining a final position and rotation of the implanted, uncorrected phakic IOL by optically measuring fiducial marks on the IOL;
(step 506) Re-measuring wavefront aberrations of the eye with the implanted, uncorrected IOL in place;
(step 508) Designing a wavefront-customized correction profile for the IOL; and
(step 510) Modifying in-vivo the implanted, un-corrected IOL with the customized correction profile, while the IOL is implanted in the eye.

Note: In the flow chart of FIG. 10, the first step 500 can optionally be omitted.

In the manufacturing step 304 of FIG. 8, if the WFG IOL is axisymmetric (rotationally-symmetric), then a standard machine lathe can be used to manufacture (turn) the IOL. However, if the WFG correction requires an off-center (offset) patch (due to XY misalignments and/or Z-axis rotations) then the WFG customized lens will be non-axisymmetric. In this latter case, a digitally-controlled lathe with fast Z-axis stage can be used to fabricate the part. The advent of fast Z-axis diamond-turned lathes has enabled the construction of parts that are non-axisymmetric. As the lathe turns through a given revolution, the tool is placed on a fast stage that can rapidly move in and out synchronized with the rotation of the part. Very accurate optical surfaces can be fabricated using single-point diamond turning. The lathe speed is adjusted to match the requirements for the Z-axis motion. This is a key enabling technology for cutting lenses that include astigmatism, as the tool is required to move in and out twice per revolution. For fabricating corrected higher-order Zernike terms, the number of motions per revolution increases, but the magnitude of the move decreases (generally). There are several companies that make such lathe tools for this kind of application and they are in common use in the ophthalmic industry. These include DAC, and Sterling-Presitec, Inc.

Alternatively, for 3-D non-axisymmetric lenses, the manufacturing step (304) can comprise using a Refractive Index VWiting (RIW) technique, which provides for local modification of the index of refraction (also known as Laser Induced Reactive Index Change, LIRIC). Clerio Vision U.S. Pat. No. [10,893,936] has shown that it is possible to modify the index of refraction of various optical polymeric materials by focusing a low-energy, focused femtosecond laser spot into the material at a very high repetition rate. The intensity of laser illumination is controlled below the threshold for ablation or damage. Scanning the focused beam across the surface results in a series of localized spots, which can converge into an internal 2-D sheet or layer of with a locally different index of refraction. This works successfully not only in various plastic or synthetic materials (PMMA, Acrylic, Silica Hydrogel, etc), but also in biological materials (human cornea, natural lens, etc). Moreover, the region of material just outside of the focal region is minimally affected by the laser light.

Alternatively, for 3-D non-axisymmetric lenses, the manufacturing step (304) can comprise using 3-D selective curing of liquid materials. Some contact lenses are made through UV curing of liquid materials, usually contained in a transparent mold. This could also be applied to the manufacture of IOLs. Since the curing of these materials is dependent on the amount of curing, the light can be precisely adjusted to control the thickness or shape of the IOL lens. Using digital projection, light patterns can be precisely controlled, which allows for fabrication of custom shapes. Material that is uncured simply flows away when the transparent mold is removed, and the cured contact lens or IOL is removed.

Alternatively, for 3-D non-axisymmetric lenses, the manufacturing step (304) can comprise using additive methods (e.g., 3-D printing), which have increasingly shown promise for fabricating arbitrary surfaces. While the accuracy has typically limited this kind of application in optics, as the technology advances it is likely that this will shortly become feasible.

Alternatively, for 3-D non-axisymmetric lenses, the manufacturing step (304) can comprise using adaptive molding U.S. Pat. No. [6,830,712]. Many contact lenses are manufactured through molding. This technique is also a viable method for IOL fabrication. Usually, molding is used to mass-produce similar shape objects. However, it is possible to make a mold where one or more surfaces are adjusted in 3-D with piezo-electric or other actuators to create a desired surface profile. A multitude of individual actuators are attached to a flexible surface that form the mold face. This technique is fundamentally limited to creating shapes that are smoothly varying but that is satisfactory for creating customized shapes for eye corrections because the necessary corrections are almost always smoothly varying.

Alternatively, for 3-D non-axisymmetric lenses, the manufacturing step (304) can comprise performing laser ablation (e.g., LASIK) and removing material from a base IOL shape. This laser ablation technique is well-suited to manufacturing non-axisymmetric IOLs.

Alternatively, for 3-D non-axisymmetric lenses, the manufacturing step (304) can comprise using a light-adjustable material. This method is known as "light adjustable lens" (LAL) and it was commercialized by Calhoun Vision. By including polymers in the IOL material that swell when exposed to light, it is possible to control the shape of the IOL, and hence its "aberration content", by selective exposure to light (usually UV light). Once the desired profile is obtained, the overall material can be "locked" by uniformly exposing the entire lens to UV light. This is commonly used to adjust the final power of the IOL after implantation in the eye to compensate for errors in final axial position. However, it could also be used for treatment of aberrations.

Figure 11A:
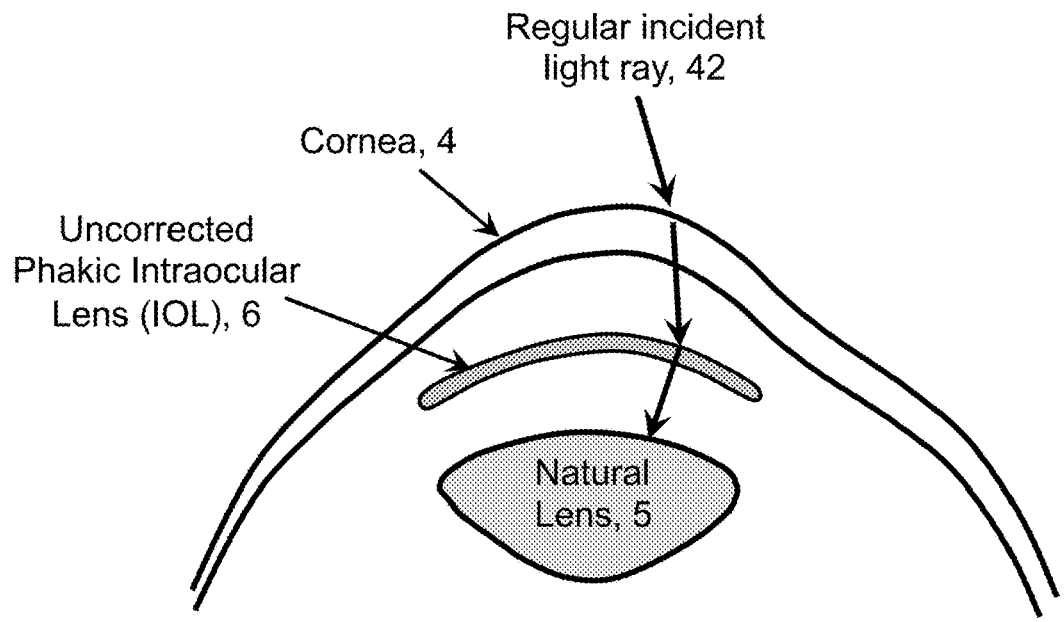
FIG. 11A shows a cross-section side view of an eye with an implanted IOL sitting above the natural lens, before in-situ wavefront correction, according to the present invention.

FIG. 11A shows a cross-section side view of an eye with an implanted phakic IOL sitting next to a natural lens 5, before wavefront correction, according to the present invention. An example of an incident light ray 42 is shown as being bent (refracted) by the cornea 4 and the IOL 6 towards the natural crystalline lens 5.

Figure 11B:
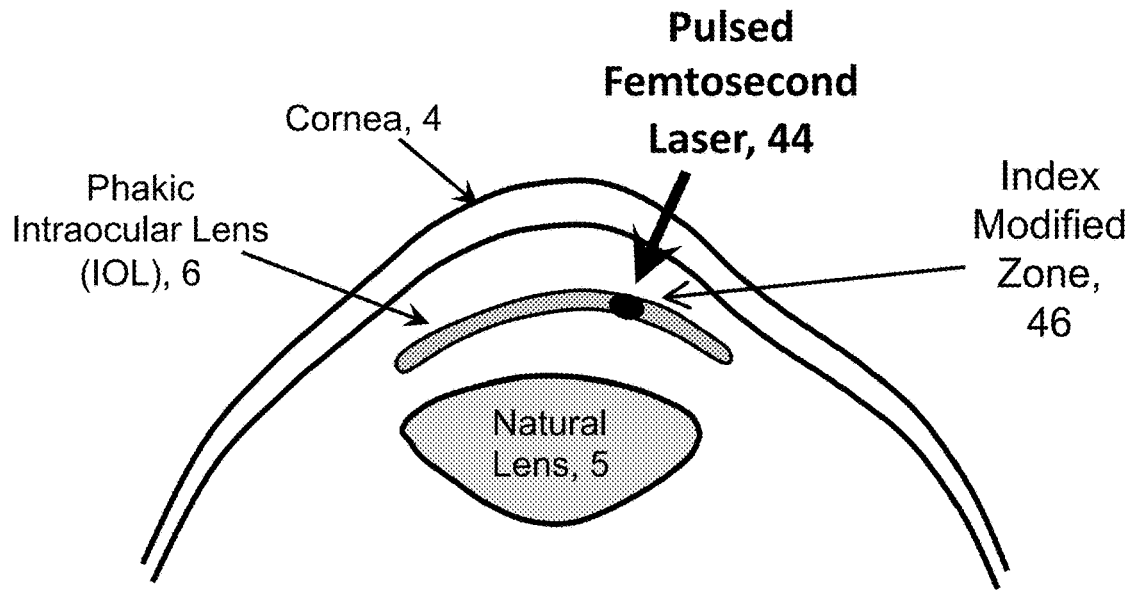
FIG. 11B shows a cross-section side view of an eye with an implanted phakic IOL, during in-situ laser wavefront correction, according to the present invention.

FIG. 11B shows a cross-section side view of an eye with an implanted phakic IOL, during in-situ femtosecond laser LIRIC treatment, according to the present invention. Here, a pulsed femtosecond laser pulse 44 is being applied to a phakic IOL 6, which creates an index-modified zone 46 that has an altered index of refraction. The pulsed FS laser spot is then scanned across the entire IOL 6 (or a portion of the IOL) depending on the amount of correction required (based on the degree and location of Higher-Order Aberrations (HOA's) as measured by the wavefront sensor (not shown)).

Figure 11C:
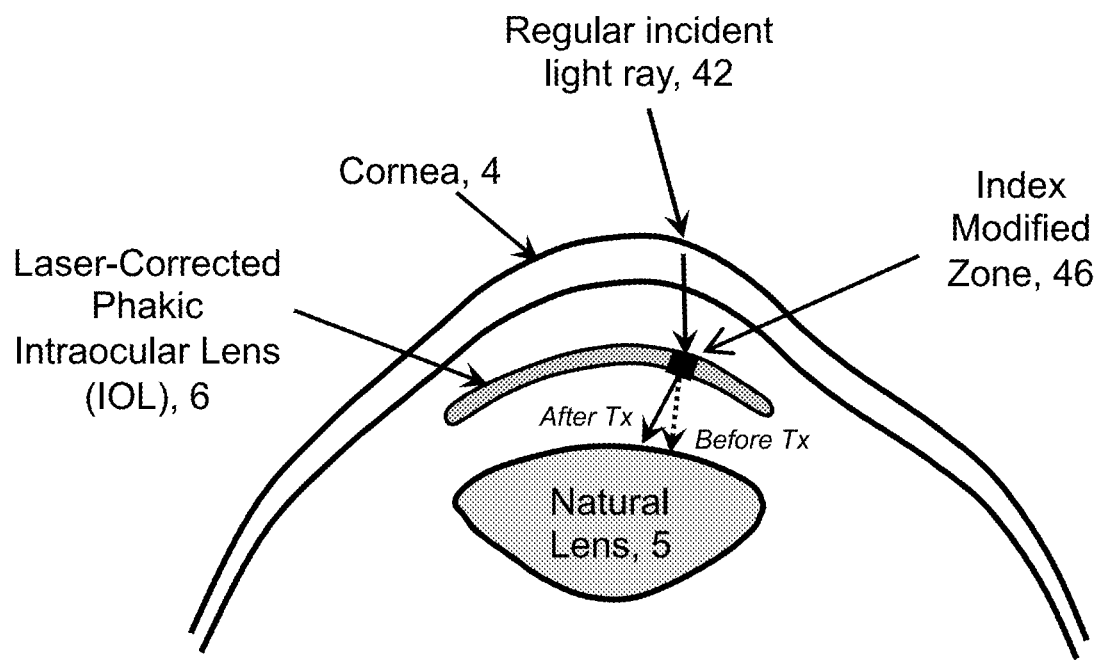
FIG. 11C shows a cross-section side view of an eye with an implanted phakic IOL, after in-situ laser wavefront correction, according to the present invention.

FIG. 11C shows a cross-section side view of an eye with an implanted phakic IOL, after performing in-situ femtosecond laser wavefront correction, according to the present invention. Here, incident light ray 42 is deflected a different amount after passing through the index-modified zone 46, due to the local change in index of refraction caused by the FS laser treatment (Tx).

In all of the embodiments of the present invention, the optical instruments can rapidly multiplex (i.e., cycle) between wavefront sensing/measurement and visual iris imaging. This allows the clinician to create a dynamic sequence of measurements with both wavefront sensing (WFS) and iris imaging being interleaved, allowing the clinician to find the position of the IOL on the eye relative to the pupil, and to measure the wavefront through the implanted IOL simultaneously (or near simultaneously).

Figure 12:
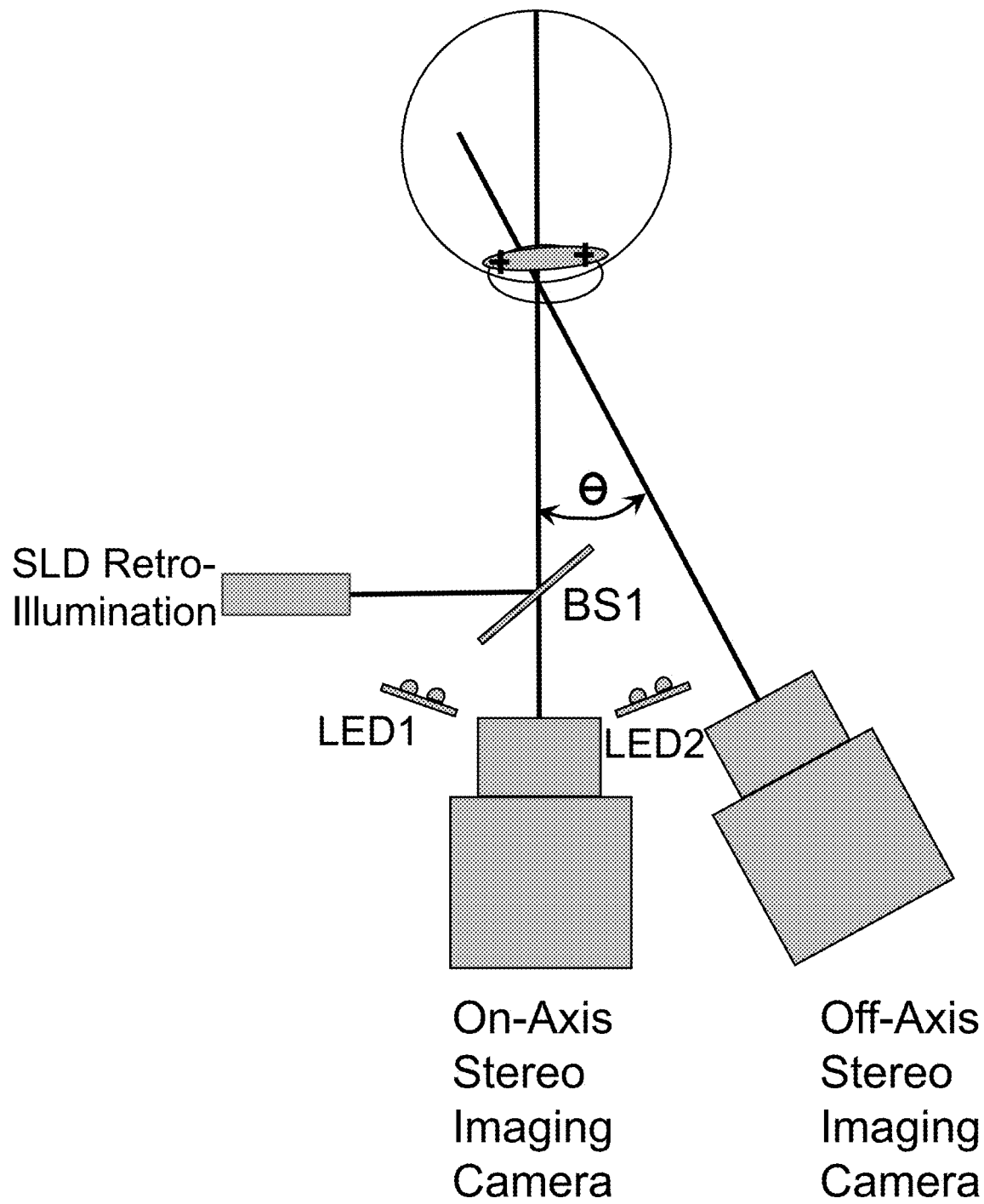
FIG. 12 shows an optical arrangement for a stereo IOL tracker that can determine IOL position (XYZ), rotation, and tip/tilt in the eye, according to the present invention.

FIG. 12 show an embodiment of a stereo eye tracking system that can be used to determine the IOL position in both XYZ directions and rotation. In this embodiment, fiducials placed on the un-corrected IOL are illuminated by retro-reflection from SLD light scattered off the retina. Retro-illumination has the advantage that changes in scattering causes light rays to be deflected, which are then clipped by apertures in the optical system (not shown). This results in a shadow or darker region in the otherwise bright field retro-illumination image. The fiducials can comprise scribe marks, diffractive laser-marked patterns, holes, or regions of the IOL that are impregnated with a dye or ink. Advantageously, an infrared absorbing ink would be used that transmits in the visible, so that they are not visible to the patient, but are readily detected in the infrared with the retro-illumination system. With the use of two or more fiducials, the XY position of the IOL can be determined. Using the stereo imaging cameras, the same features can be imaged at an angle to the normal optical axis (at an angle of approximately 30°). This allows for triangulation to determine the Z-axis position. For some index writing methodologies, this path may not be necessary since the Z-position of the index surface is not important to achieve the desired effect.

The tilt of the surface is measured using Purkinje reflections from the surface of the IOL. The location of these Purkinje images is very sensitive to tip and tilt of the IOL. While in general these images may overlap and make image processing somewhat challenging, the illuminating LEDs can be turned on sequentially in synchronization with the global shutter cameras, and thus minimize the confusion.

The system for tracking the fiducials and Purkinje images can be used to provide real-time feedback to the laser writing system that is used to create the in-situ index changes necessary to correct for the aberration(s). In the simplest implementation, the system can be used to disable the laser when the error in position or tilt exceeds some threshold, or it can be used in a more sophisticated, closed-loop fashion to control the steering mirrors that direct the writing laser.

While this system can monitor the XYZ, rotation and tip/tilt of the IOL in the eye in real time, it must be combined with the writing laser path to be effective. That means that it must be integrated with the laser delivery system, which needs to incorporate optics for delivering and controlling the laser to write the aberration patterns. In addition, a femtosecond laser writing system must control the eye's position carefully to deliver the laser energy in precise locations, with minimum distortions caused by the cornea itself. To this end the eye can be constrained with an eye interface system, which can include a suction ring to hold the eye in a fixed position and align it to the laser delivery system, and a liquid or flexible eye interface to compensate for aberrations in the cornea so that the laser can be focused properly.

Figure 13:
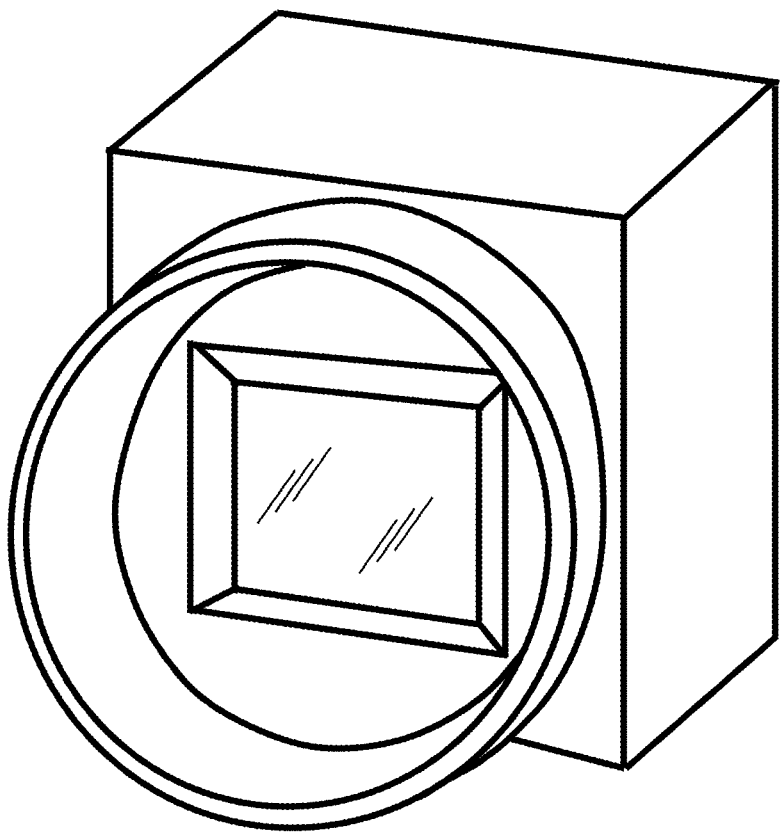
FIG. 13 shows an isometric photograph of an example of CCD imaging camera: Model # Sentec STC-MCCM200U3V, 2048×1088, 167 fps, according to the present invention.

FIG. 13 shows a photograph of an example of a CCD imaging camera: Model # Sentec STC-MCCM200U3V, 2048×1088, 167 fps, according to the present invention. Frame rates up to 465 fps of full frame camera systems can be used.

Figure 14:
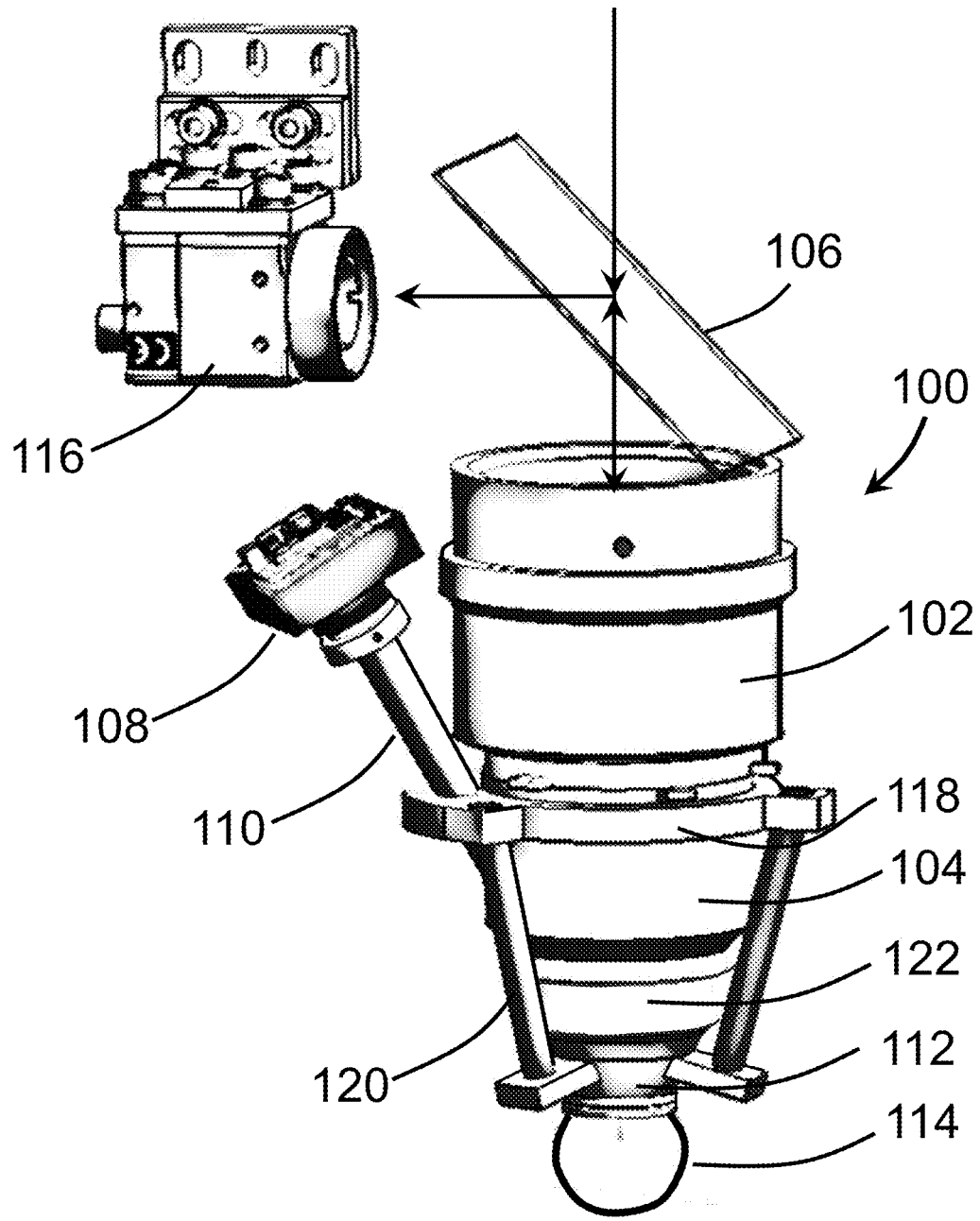
FIG. 14 shows a 3-D, solid-shaded, perspective view of an adapter means for incorporating the IOL tracker system into a patient interface with liquid interface for compensating for corneal aberrations, according to the present invention.

FIG. 14 shows a 3-D solid-shaded perspective view of a mechanical camera adapter means 100 for incorporating the stereo IOL tracker system into a patient interface with liquid interface (112) for compensating for corneal aberrations, according to the present invention, while providing for the tracking system described previously. The on-axis tracking camera 116 is incorporated using a dichroic beamsplitter 106 to separate return images from the laser path. Imaging optics may share one objective lens, but may use other lenses to create the appropriate image relay. The illumination LEDs (not shown) are incorporated into the patient interface adapter itself, and the stereo imaging camera 116 is mounted at an off-axis angle (approximately 30°) to the central axis of adapter 100. Adapter 100 comprises a lower cylindrical barrel 104, and an objective lens 102, which serves as both an imaging lens for the imaging camera 116 and for focusing the femtosecond laser light that passes through beamsplitter 106. Three support rods 120, 120', 120" mechanically support structural ring 118, which holds hollow tube 110 that connects off-axis imaging camera 108 to adapter 100. Eyeball 114 can be seen in this Figure, held in place by eye interface suction ring 112.

Figure 15:
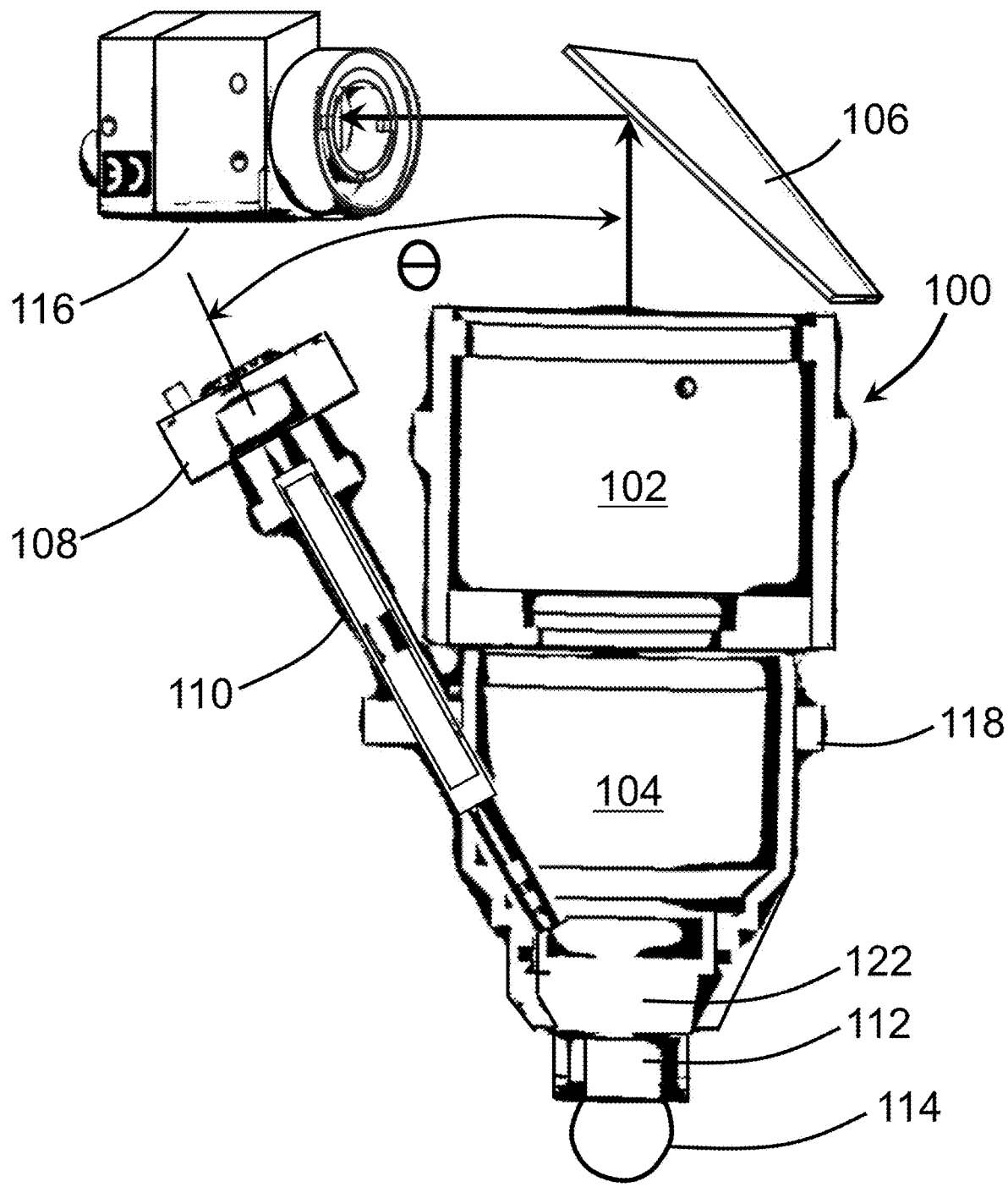
FIG. 15 shows a cross-section elevation view of an adapter means for incorporating the IOL tracker system into a patient interface, with a liquid interface for compensating for corneal aberrations, according to the present invention.

FIG. 15 shows a cross-section elevation view of the mechanical camera adapter means 100 for incorporating the stereo IOL tracker system into a patient interface with an innovative liquid interface (112) for compensating for corneal aberrations, according to the present invention. The eye interface 112 has several parts, including a suction ring 212 to hold the assembly in place on the eye, an internal cell 112 to hold the liquid (preferably saline), and a window 210 that seals the liquid chamber. The window 210 has a convex lower surface so that any bubbles or excess fluid are pushed out of the optical region.

Figure 16:
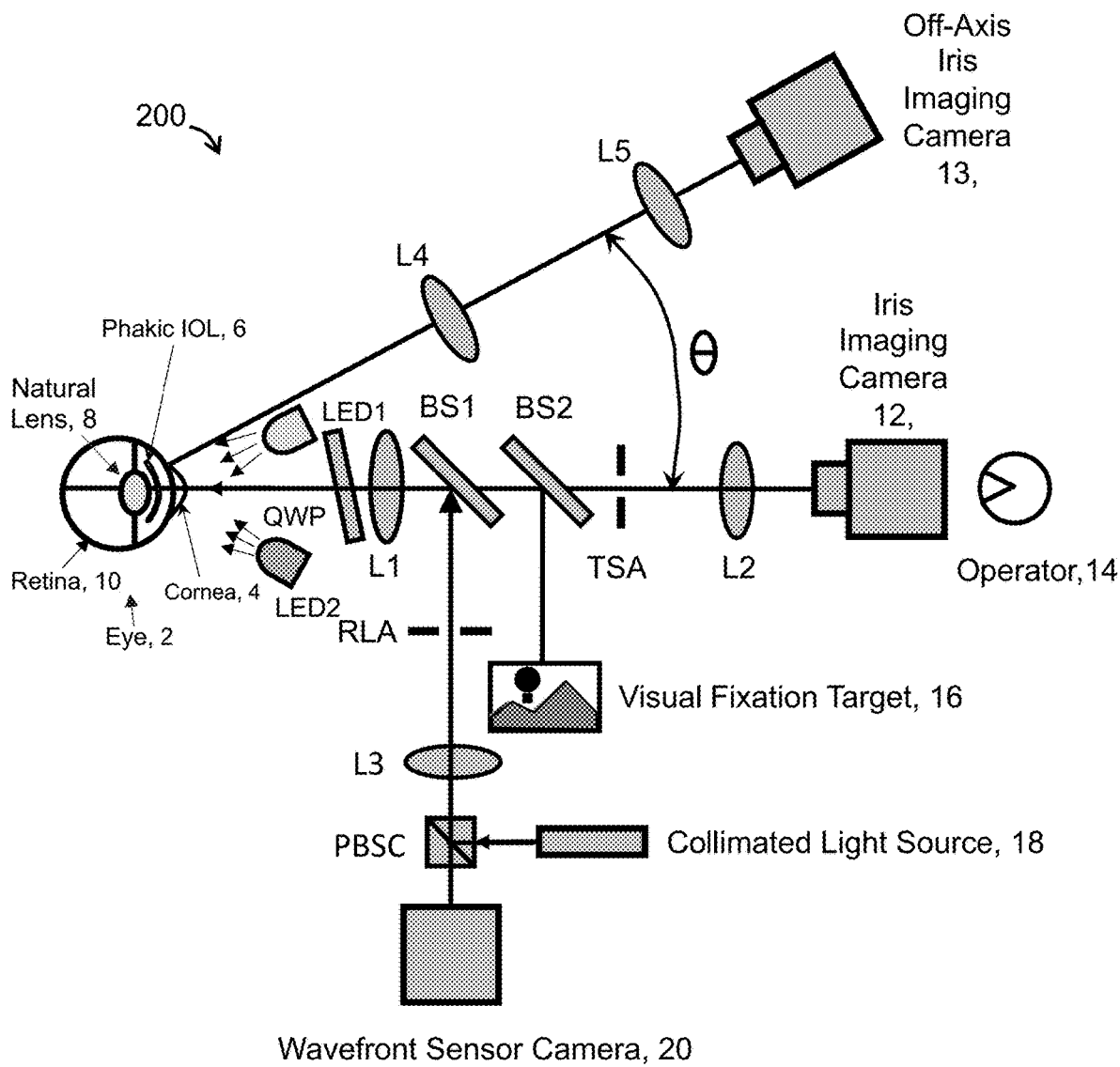
FIG. 16 shows a schematic optical layout of a stereo aberrometer, which is a combination of the basic aberrometer shown in FIG. 1 and the Off-Axis Camera Adapter shown in FIGS. 14 and 15, according to the present invention.

FIG. 16 shows a schematic optical layout of a stereo aberrometer, which is a combination of the basic aberrometer shown in FIG. 1 and the Off-Axis Camera Adapter shown in FIGS. 14 and 15, according to the present invention. FIG. 16 shows the off-axis iris imaging camera 13 disposed at an off-axis angle of approximately 30° (other angles can be used, as well). The off-axis imaging path contains a pair of lenses, L4 and L5, which also form a telecentric teleobjective (like lenses L1 and L2 for the on-axis iris imaging camera). If the lenses L4 and L5 are made small in diameter for mechanical convenience, optionally a field lens can be added in between L4 and L5 to improve light gathering efficiency. This is a common modification used in rifle scopes. An alternative to adding a field lens is just to make the lens diameters L4 and L5 a bit larger.

Figure 17:
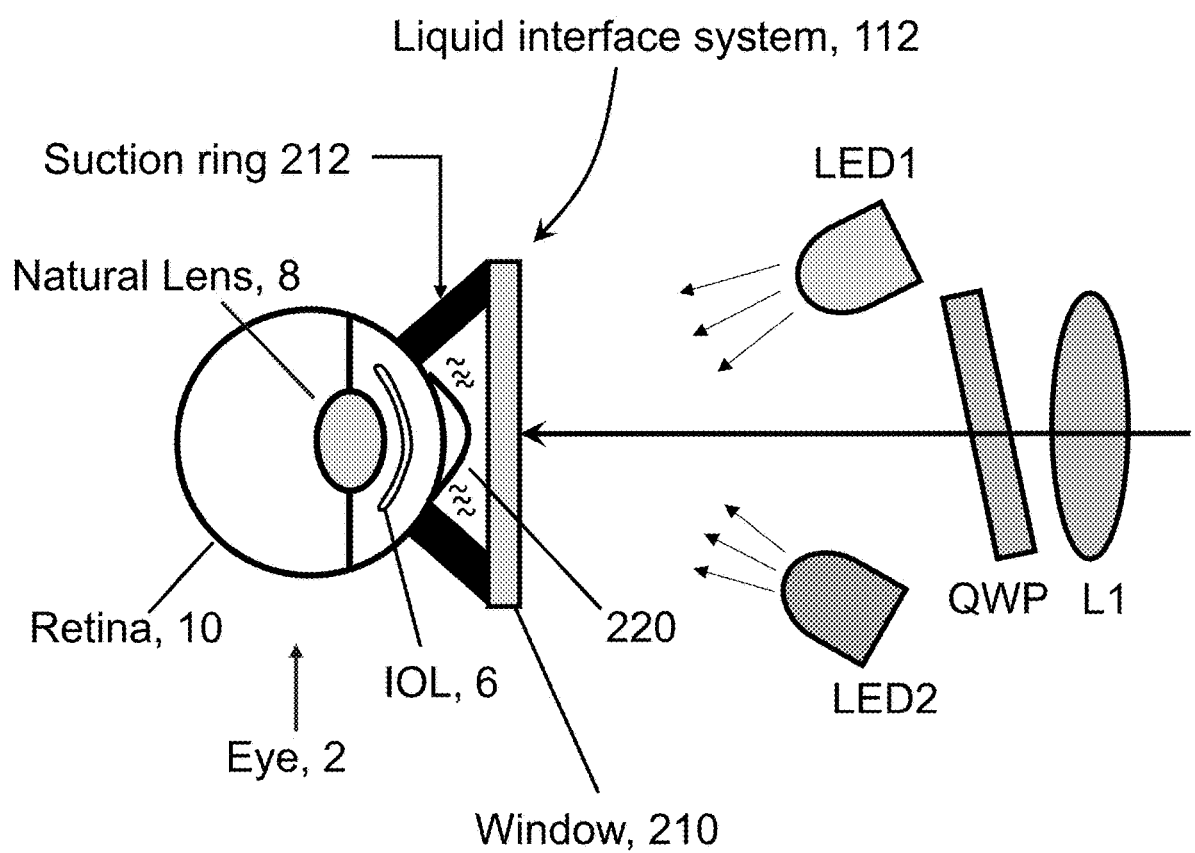
FIG. 17 shows an enlarged schematic optical layout of a stereo aberrometer, which is a combination of the basic aberrometer shown in FIG. 1 and the Off-Axis Camera Adapter shown in FIGS. 14 and 15, according to the present invention.

FIG. 17 shows an enlarged schematic optical layout of a stereo aberrometer, which is a combination of the basic aberrometer shown in FIG. 1 and the Off-Axis Camera Adapter shown in FIGS. 14 and 15, according to the present invention. In this enlarged view of the proximal end of the Off-Axis Camera Adapter, the eye 2 is held steady by an eye interface system 112, which is held in place by a suction ring 212. Transparent window 220 is attached to suction ring 212; and the volume defined by the window 220, the suction ring 212, and the outer periphery of the eye 2 is filled with saline water 220. Both the on-axis iris imaging camera and the off-axis iris imaging camera look at eye 2 through window 210. The presence of saline water inside the liquid interface cup 112 provides an index of refraction that compensates for any corneal aberrations.

Figure 18:
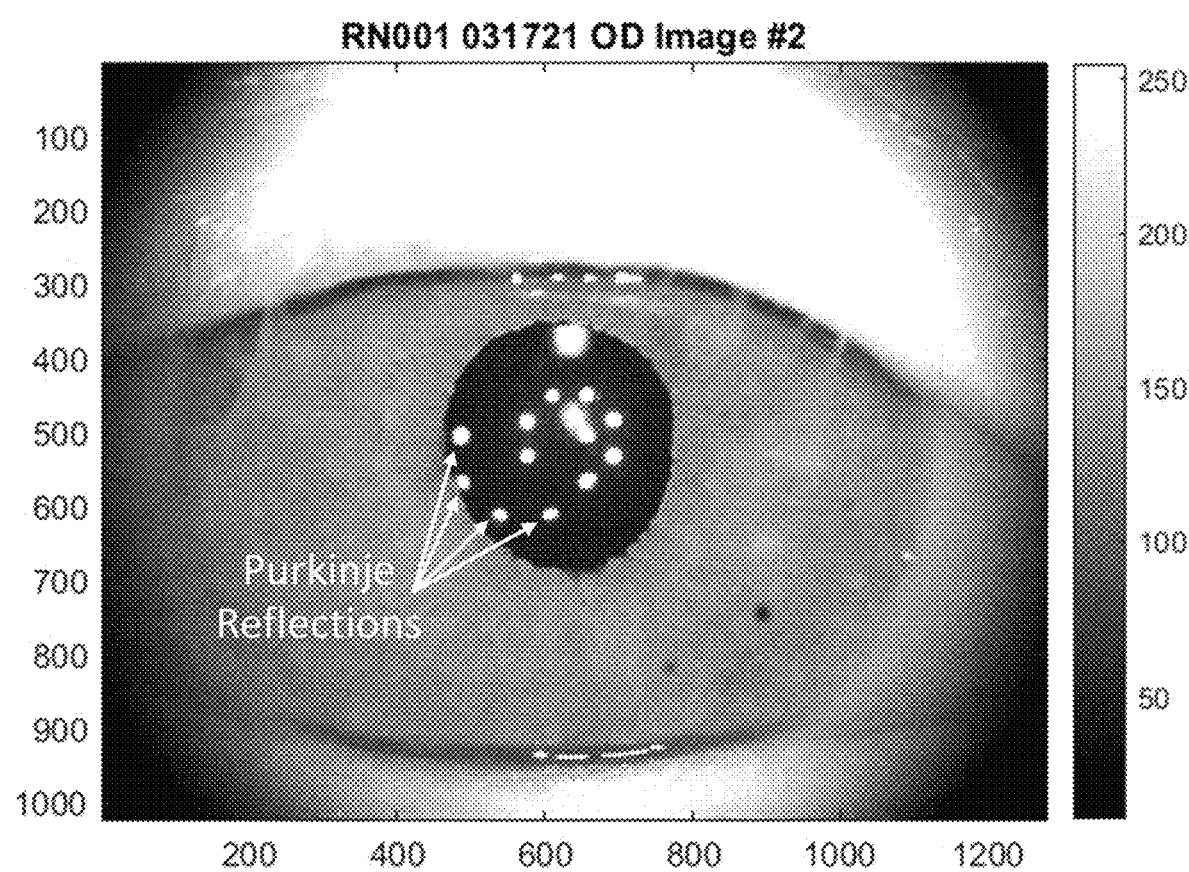
FIG. 18 shows a typical photograph of an eye being examined by an optical instrument, showing Purkinje reflection images, according to the present invention.

FIG. 18 shows a photograph of an eye being examined by an optical instrument, according to the present invention, showing both inverted and regular images of Purkinje reflections from the cornea and from the implanted IOL inside the eye. The mis-rotation angle and XY mis-position shift of the implanted IOL can be derived from on-is image information. The Z-axis position of the IOL needs additional measurement, which is provided by triangulating the images taken by the stereo pair of iris imaging cameras.

Stereo Purkinje Imaging

The stereo Purkinje imaging concept of the present invention comprises the following actions (in no particular order):
1. Viewing Purkinje reflections from an implanted IOL using both on-axis and off-axis imaging cameras that are configured as a stereo pair of cameras;
2. Sequencing (synchronizing) light sources with global shutter camera(s) to determine the source(s) of Purkinje reflections;
3. Using fiducial marks and/or IOL edge detection for enhancing real-time XY tracking of the IOL;
4. Deriving angle and XY mis-alignment information about an implanted IOL from on-axis information;
4. Using Purkinje reflections for tracking tip/tilt and XY mis-alignments of the IOL ($P_1$ is used for eye/cornea, $P_3$ & $P_4$ is used for IOL position).
5. Using triangulation between the pair of stereo imaging cameras to track the IOL's Z-axis position;
6. Using retroreflection to enhance fiducial detection; and
7. Using retro-illumination to enhance determination of the position of rings in Multi-Focal IOLs.

Another embodiment of a method for correcting aberrations in an eye that uses a wavefront-customized phakic or pseudophakic intraocular lens (IOL) comprises performing the following steps, in the order listed:
(1) designing and fabricating a phakic or pseudophakic intraocular lens that corrects for a base refraction of the eye;
(2) implanting the lens in the eye;
(3) measuring the wavefront aberrations of the eye including the implanted lens; and
(4) modifying the aberrations of the implanted intraocular lens in-vivo.

Another embodiment of an optical instrument for tracking and treating an eye in-vivo comprises:
(a) a femtosecond laser system for delivering low energy pulses to an eye;
(b) an eye interface system for fixing the eye; and
(c) a tracking system for determining and monitoring one or more positions of an IOL.

We claim:

1. A method for correcting higher-order aberrations in an eye that uses a wavefront-customized phakic or pseudophakic intraocular lens (IOL), comprising the following steps, in the order presented:
(1) measuring one or more higher-order aberrations of a bare eye with a wavefront aberrometer;
(2) designing a 3-D wavefront-customized correction profile for an IOL based on measured results from the wavefront aberrometer in step (1);
(3) fabricating a 3-D customized IOL that incorporates the 3-D wavefront-customized correction profile;
(4) implanting the 3-D wavefront-customized IOL into the eye; and
(5) adding one or more fiducial marks onto the IOL in step (3) that act as location features to aid in the proper alignment of the IOL.

2. The method of claim 1, further comprising:
step (5) leaving a natural crystalline lens in place after step (4).

3. The method of claim 1, wherein fabricating the 3-D customized IOL in step (3) comprises using a precision lathe machine with a diamond tool bit that has a fast Z-axis stage.

4. The method of claim 1, wherein fabricating the 3-D customized IOL in step (3) comprises locally changing the index of refraction of the IOL's material with a low-energy, high repetition rate, scanned, pulsed femtosecond laser beam before the IOL or a contact lens is implanted in the patient's eye in step (4).

5. The method of claim 1, wherein fabricating the 3-D customized IOL in step (3) comprises locally changing the index of refraction of the IOL's material with a low-energy, high repetition rate, scanned, pulsed femtosecond laser beam after the IOL or a contact lens has been implanted in the patient's eye in step (4).

6. The method of claim 1, further comprising, before the IOL is implanted, using a femtosecond laser to create diffractive fiducial marks comprising a plurality of uniformly-spaced holes or lines that scatter light preferentially more strongly for certain incident angles and color combinations.

7. The method of claim 1, wherein step (3) comprises using a non-axisymmetric, 3-D manufacturing technique selected from the group consisting of: 3-D selective curing of a liquid material, 3-D additive printing, 3-D adaptive molding, 3-D light-adjusted material fabrication, and combinations thereof.

8. A method of using an optical eye tracking instrument for dynamically measuring eye parameters, and for using a 3-D wavefront-customized phakic or pseudophakic intraocular lens (IOL) for correcting a person's vision, comprising the following steps, in the order presented:
   (1) measuring wavefront aberrations of a bare eye with a wavefront aberrometer;
   (2) implanting an uncorrected IOL into the eye;
   (3) determining a final position of the implanted, uncorrected IOL by optically measuring one or more fiducial marks located on the IOL;
   (4) designing a 3-D wavefront-customized correction profile for the implanted IOL; and
   (5) modifying in-vivo the un-corrected IOL with the 3-D wavefront-customized correction profile after the IOL has been implanted in the eye.

9. The method of claim 8, wherein step (3) comprises using stereo triangulation to determine a Z-axis position of the IOL by comparing an on-axis iris image taken by an on-axis iris imaging camera to an off-axis iris image taken by an off-axis iris imaging camera.

10. The method of claim 8, wherein step (5) further comprises locally changing an index of refraction of the IOL's material by using a scanning femtosecond laser to locally modify the index of refraction of the IOL.

11. The method of claim 10, further comprising performing the following step in-between steps (3) and (4), comprising: re-measuring one or more wavefront aberrations of the eye after the uncorrected IOL has been implanted in the eye.

12. The method of claim 8, wherein the eye tracking instrument comprises a first off-axis light source, LED1, that emits light at a first wavelength, and a second off-axis light source, LED2, that emits light at a second wavelength, that is measurably different than the first wavelength.

13. The method of claim 8, further comprising determining the XY mis-position and tip/tilt mis-rotation of an implanted IOL by using dark field imaging with a pair of off-axis illumination sources to measure a position and a size of the eye's sulcus and ciliary body.

14. The method of claim 13, further comprising using software subtraction of two adjacent iris images (from a sequence of captured images) to generate a dark field image of the eye, by comparing a pair of alternating images captured when either one illumination light source is ON, while the other (opposing) light source is OFF.

15. A method for correcting higher-order aberrations in an eye that uses a wavefront-customized phakic or pseudophakic intraocular lens (IOL), comprising the following steps, in the order presented:
   (1) measuring one or more higher-order aberrations of a bare eye with a wavefront aberrometer;
   (2) designing a 3-D wavefront-customized correction profile for an IOL based on measured results from the wavefront aberrometer in step (1);
   (3) fabricating a 3-D customized IOL that incorporates the 3-D wavefront-customized correction profile;
   (4) implanting the 3-D wavefront-customized IOL into the eye; and
   (5) using Purkinje reflection images to determine XY mis-alignment and tip/tilt mis-rotation of the implanted IOL.

16. A method for correcting aberrations in an eye that uses a wavefront-customized phakic or pseudophakic intraocular lens (IOL), comprising the following steps, in the order listed:
   (1) designing and fabricating a phakic or pseudophakic intraocular lens that corrects for a base refraction of the eye;
   (2) implanting the intraocular lens in the eye;
   (3) measuring wavefront aberrations of the eye including the implanted lens;
   (4) modifying in-vivo the aberrations of the implanted intraocular lens; and
   (5) using fiducial marks to locate an IOL's XY position relative to the eye during step (4).

17. The method of claim 16, wherein step (4) comprises using a laser index writing technique to modify the aberrations of the IOL.

18. The method of claim 17, wherein the laser index writing technique comprises using a low-energy femtosecond laser system.

19. The method of claim 17, further comprising controlling the laser index writing technique by monitoring the position of the IOL during the procedure.

20. The method of claim 16, further comprising using Purkinje reflections from the IOL to measure tip/tilt angles of the IOL relative to the eye during step (4).

21. The method of claim 16, further comprising using a light-adjustable-lens modification technique during step (4).

22. An optical instrument used for improving a person's vision, comprising a combined aberrometer, corneal topographer, and iris imaging camera, wherein the optical instrument comprises three paths:
   (1) an on-axis iris imaging path;
   (2) a wavefront sensor path; and
   (3) a fixation target path;
wherein the on-axis iris imaging path #1 comprises:
   (a) a plurality of off-axis illumination sources arranged to directly illuminate an eye;
   (b) a quarter wave plate (QWP);
   (c) a pair of beam splitters;
   (d) a pair of lenses, LENS1 and LENS2, configured as a telecentric teleobjective in the iris imaging path;
   (e) a telecentric stop (TSA) disposed in-between LENS1 and LENS2; and
   (f) an on-axis iris imaging camera; and
wherein the wavefront sensor path #2 comprises:
   (i) a wavefront sensor camera;
   (ii) a collimated light source;
   (iii) a polarizing beam splitting cube;
   (iv) a third lens; and
   (v) a Range Limiting Aperture (RLA); and
wherein the fixation target path #3 comprises a micro-video-display fixation target.

23. An optical instrument for tracking and treating an eye in-vivo comprising:
   (a) a femtosecond laser system for delivering low energy pulses to an eye;
   (b) an eye interface system for fixing the eye; and
   (c) a tracking system for determining and monitoring one or more positions and tilts of an IOL;
   wherein the tracking system comprises:
      (a) an off-axis iris imaging camera with optical image relay lens;
      (b) an on-axis iris imaging system; and
      (c) a plurality of illumination light sources disposed around a periphery of the on-axis iris imaging system; and wherein the one or more positions and tilts of the IOL are determined by comparing and analyzing images captured from both the on-axis iris imaging system and the off-axis iris imaging camera.

24. The optical instrument of claim 23, wherein the eye interface system comprises a suction ring attached to a transparent window, with saline water filling a volume defined by the suction ring, the window, and a periphery of the eye being examined.

25. The optical instrument of claim 23, comprising optical means for dynamically tracking fiducials on an IOL with both the on-axis iris imaging system and the off-axis iris imaging camera.

26. The optical instrument of claim 23; wherein the femtosecond laser is introduced through a dichroic beamsplitter.

27. The optical instrument of claim 23, wherein the tracking system comprises a dark field mask (DFM) that has a central obscuration optic that blocks light travelling along a central zone of a main optical path.

28. The optical instrument of claim 23, wherein the tracking system further comprises a small motor for switching the optical instrument between a telecentric stop and a dark field mask (DFM).

29. The optical instrument of claim 23, wherein the tracking system further comprises a programmable spatial light modulator (SLM) optical component to enhance fiducial imaging.

30. The optical instrument of claim 23, wherein the tracking system further comprises a wavelength multiplexed mask (WMM) optical component that:
  (1) passes a first wavelength and blocks a second wavelength through a central circular zone of the WMM mask; and that
  (2) blocks the first wavelength and passes the second wavelength in an annular zone of the WMM mask.

* * * * *